United States Patent [19]

Newlander et al.

[11] Patent Number: 6,127,489

[45] Date of Patent: Oct. 3, 2000

[54] SILYL LINKER FOR SOLID PHASE ORGANIC SYNTHESIS OF ARYL-CONTAINING MOLECULES

[75] Inventors: Kenneth A. Newlander, West Chester; Michael L. Moore, Media, both of Pa.

[73] Assignee: SmithKline Beecham Corporation, Philadelphia, Pa.

[21] Appl. No.: 09/194,091

[22] PCT Filed: May 20, 1997

[86] PCT No.: PCT/US97/08557

§ 371 Date: Nov. 20, 1998

§ 102(e) Date: Nov. 20, 1998

[87] PCT Pub. No.: WO97/44367

PCT Pub. Date: Nov. 27, 1997

Related U.S. Application Data

[60] Provisional application No. 60/017,955, May 20, 1996.

[51] Int. Cl.$^7$ ........................................................ C08F 8/00
[52] U.S. Cl. ..................... 525/342; 525/333.3; 525/333.6
[58] Field of Search ................................. 525/333.3, 342, 525/333.6

[56] References Cited

U.S. PATENT DOCUMENTS 4,912,170  3/1990  Niwa et al. .............................. 525/337
4,933,391  6/1990  Long et al. .............................. 525/106

*Primary Examiner*—Rachel Gorr
*Attorney, Agent, or Firm*—Nora Stein-Fernandez; Stephen Venetianer; Charles M. Kinzig

[57] ABSTRACT

This invention relates to improved silyl linkers, methods for their preparation and their use in the solid phase synthesis of aromatic carbocycles, especially electron deficient aromatic carbocycles.

22 Claims, 2 Drawing Sheets

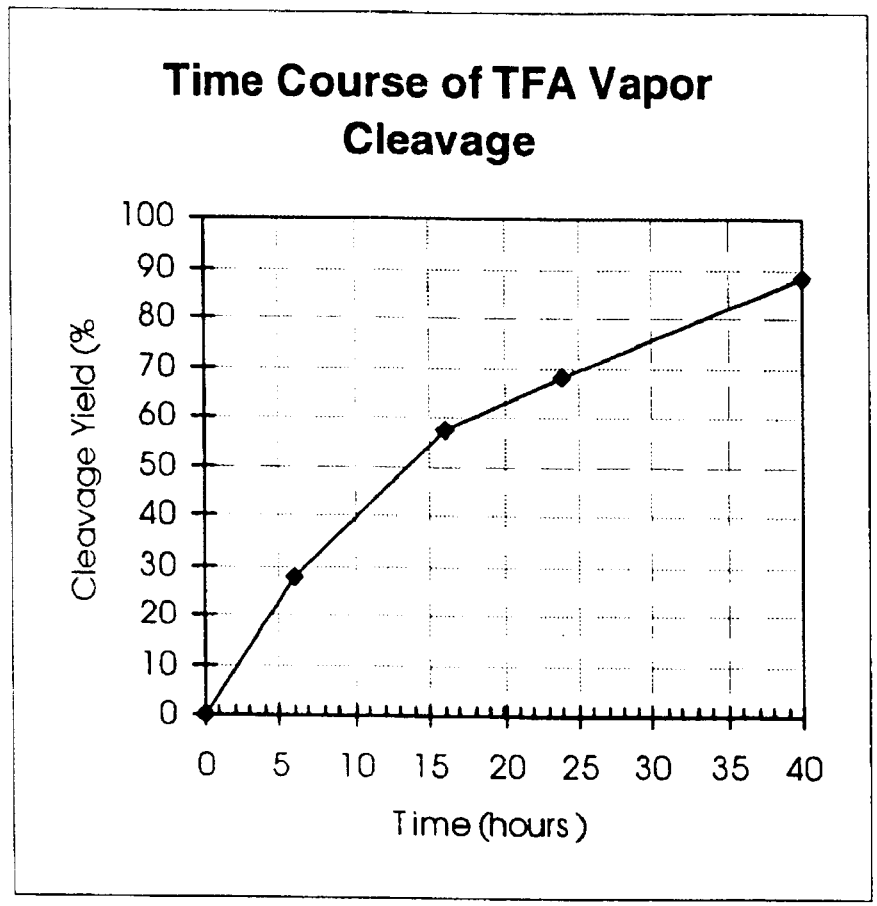
Figure 1. Time course of TFA cleavage of 2-Scheme 5

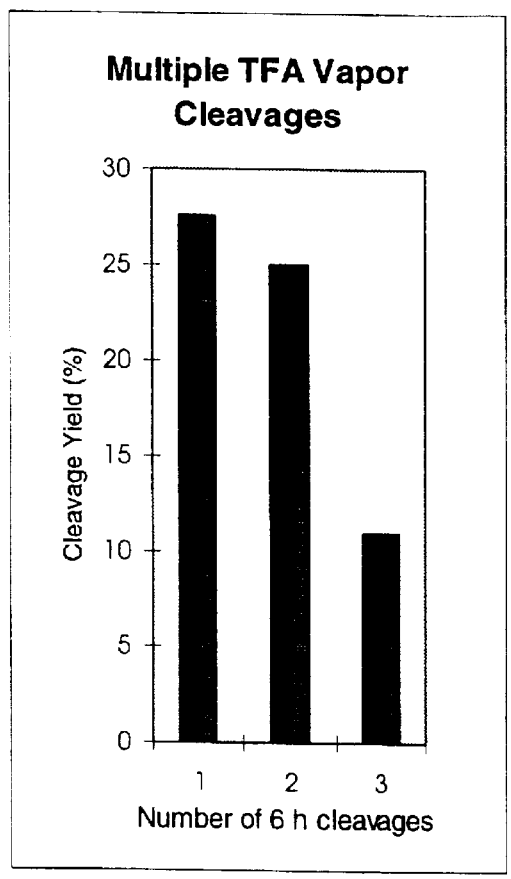
Figure 2. Yields from repeated vapor phase cleavage of an aliquot of 2-Scheme 5.

SILYL LINKER FOR SOLID PHASE ORGANIC SYNTHESIS OF ARYL-CONTAINING MOLECULES

This application claims the benefit of U.S. Provisional Application No. 60/017,955, filed May 20, 1996.

FIELD OF THE INVENTION

This invention relates to improved silyl linkers, methods for their preparation and their use in the solid phase synthesis of aromatic carbocycles, especially electron deficient aromatic carbocycles.

BACKGROUND OF THE INVENTION

In the continuing search for new chemical moieties that can effectively modulate a variety of biological processes, the standard method for conducting a search is to screen a variety of pre-existing chemical moieties, for example, naturally occurring compounds or compounds which exist in synthetic libraries or databanks. The biological activity of the pre-existing chemical moieties is determined by applying the moieties to an assay which has been designed to test a particular property of the chemical moiety being screened, for example, a receptor binding assay which tests the ability of the moiety to bind to a particular receptor site.

In an effort to reduce the time and expense involved in screening a large number of randomly chosen compounds for biological activity, several developments have been made to provide libraries of compounds for the discovery of lead compounds. The chemical generation of molecular diversity has become a major tool in the search for novel lead structures. Currently, the known methods for chemically generating large numbers of molecularly diverse compounds generally involve the use of solid phase synthesis, in particular to synthesize and identify peptides and peptide libraries. See, for example, Lebl et al., *Int. J. Pept. Prot. Res.*, 41, p. 201 (1993) which discloses methodologies providing selectively cleavable linkers between peptide and resin such that a certain amount of peptide can be liberated from the resin and assayed in soluble form while some of the peptide still remains attached to the resin, where it can be sequenced; Lam et al., *Nature,* 354, p. 82 (1991) and (WO 92/00091) which disclose a method of synthesis of linear peptides on a solid support such as polystyrene or polyacrylamide resin; Geysen et al., *J. Immunol. Meth.,* 102, p. 259 (1987) which discloses the synthesis of peptides on derivatized polystyrene pins which are arranged on a block in such a way that they correspond to the arrangement of wells in a 96-well microtiter plate; and Houghten et al., *Nature,* 354, p. 84 (1991) and WO 92/09300 which disclose an approach to de novo determination of antibody or receptor binding sequences involving soluble peptide pools.

The major drawback, aside from technical considerations, with all of these methods for lead generation is the quality of the lead. Linear peptides historically have represented relatively poor leads for pharmaceutical design. In particular, there is no rational strategy for conversion of a linear peptide into a non-peptide lead. As noted above, one must resort to screening large databanks of compounds, with each compound being tested individually, in order to determine non-peptide leads for peptide receptors.

In this respect, there has been increasing interest in the application of solid phase synthesis to the preparation of organic compounds, especially in the context of combinatorial chemistry and multiple simultaneous synthesis. One of the limitations in the solid phase approach involves the linker by which the organic molecule is attached to the solid support. Most linkers are based on protecting group chemistry and require the presence of an appropriate functional group in the target molecules being synthesized. Recently Plunkett and Ellman, *J. Org. Chem.* 1995, 60, 6006–6007 and Chenera et al., *J. Amer. Chem. Soc.* 1995, in press (see also, WO 95/16712 published Jun. 22, 1995), have described resin-bound aryl silane intermediates (1 and 2 shown below, wherein PS represents the polystyrene matrix and R represents the rest of the organic molecule synthesized on the resin) in which the aryl silane bond is cleaved by strong acid or fluoride ion to release the unfunctionalized aryl moiety.

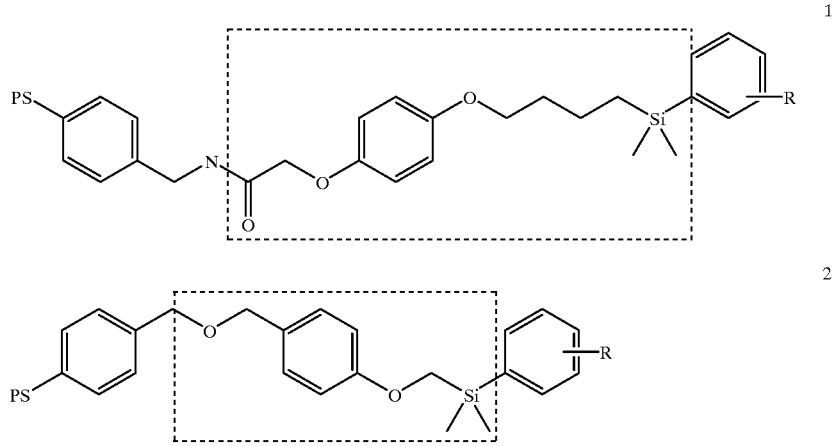

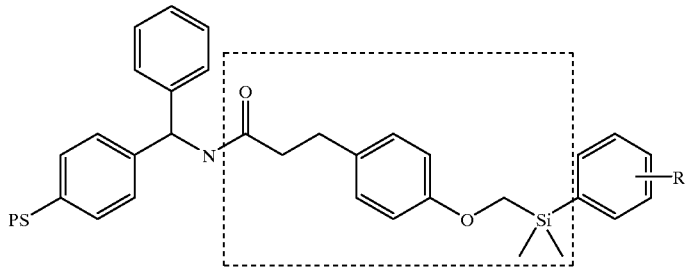

3

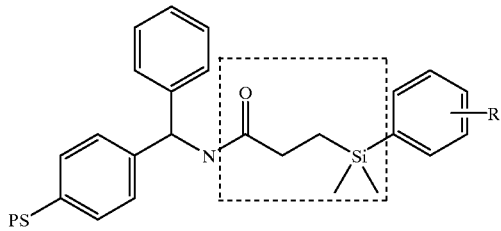

4

A modified version (see dotted box of resin-bound aryl silane intermediate 3, above) of Chenera linker 2 was used in preparing an election deficient aromatic carbocycle as shown in Scheme 1 (Compound 4-Scheme 1). However, by using modified linker 3, an unexpected alternate synthetic route was taken and the desired election deficient aromatic carbocycle 4-Scheme 1 was not recovered after neat TFA cleavage from the resin. Since the use of neat TFA for cleaving aromatic carbocycles from a resin-bound aryl silane intermediate presents several synthetic advantages, the need for a silane linker useful in solid phase synthesis for preparing election deficient aromatic carbocyles which can be cleaved from a polymeric resin by neat TFA was demonstrated. As a result, the improved aryl silane linker described herein was designed.

SUMMARY OF THE INVENTION

This invention relates to an improved novel silicon-based linker and polymer resin and methods for preparing said linker and resin. The improved linker is particularly useful in the solid phase preparation of aromatic carbocycles which contain election withdrawing substituents. By utilizing the instant linker, solid phase synthesis of a single aromatic carbocycle or a combinatorial library of derivatized aromatic carbocycles, especially where the aromatic carbocycles are electron deficient, is effectuated in that such carbocycles are easily cleaved from the resin-bound aryl silane intermediates so formed, by acid catalyzed protodesilylation, e.g., with neat TFA.

One aspect of this invention relates to methods for preparing a compound by resin-bound synthesis, wherein the compound is an aromatic carbocycle comprising an aromatic carbon atom and at least one substituent X, A, B or C that is not hydrogen or alkyl, said aromatic carbon atom having a hydrogen bound to it after cleavage from the resin. It will be recognized that the instant linker may be used in the solid phase synthesis of a plurality of aromatic carbocycles using combinatorial or multiple simultaneous synthesis methods known to the skilled artisan.

The aromatic carbocycles prepared using the improved silyl linker may be useful as receptor ligands, particularly G-protein coupled receptor ligands, enzyme inhibitors and channel blockers.

DETAILED DESCRIPTION OF THE INVENTION

BRIEF DESCRIPTION OF FIGURES

FIG. 1: Shows the time course of vapor phase TFA cleavage of 2-Scheme 5.

FIG. 2: Shows yields from repeated vapor phase cleavage of an aliquot of 2-Scheme 5.

The term "core structure(s)" is used herein at all occurrences to mean a core molecular structure(s) which is derived from compounds which have been shown to interact with a receptor, in particular, a G-protein coupled receptor, and which is used as a template for designing the libraries of compounds to be made. Core structures may be aromatic carbocycles as defined below.

The term "library of compounds" is used herein at all occurrences to mean a series or plurality of compounds derivatized from their core structure. Suitably, the core structure used for designing a library of compounds is an aromatic carbocycle. The libraries of compounds are useful as screening tools for generating lead compounds which are pharmacophores that can be further modified pursuant to a drug discovery effort.

The term "combinatorial library" is used herein at all occurrences to mean a collection of compounds based upon a core structure, for example, an aromatic carbocycle structure, wherein the library contains a discrete number of independently variable substituents, functional groups or structural elements, and further, wherein the library is designed so that, for the range of chemical moieties selected for each of the independently variable substituents, compounds containing all possible permutations of those substituents will be present in the library. Thus, by way of illustration, if a core structure, labeled R, contains three independently variable substituents, labeled X, Y and Z, and if X is taken from m different chemical moieties, Y from n different chemical moieties and Z from p different chemical moieties (wherein m, n and p are integers which define the size of the library, and which range between 1 to 1000; preferably between 1 to 100; most preferably between 1 to 20), then the library would contain m×n×p different chemical compounds and all possible combinations of X, Y and Z would be present on the core structure R within that library. The methods for preparing combinatorial libraries of compounds are such that the molecularly diverse compound members of the libraries are synthesized simultaneously.

The term "aromatic carbocycle" is used herein at all occurrences to mean a compound which comprises a single ring or a fused ring system, preferably 5–14 membered ring systems, and, for purposes herein, includes an optionally substituted biphenyl, composed of carbon atoms having aromatic character, e.g., characterized by delocalized electron resonance and the ability to sustain a ring current and which ring or ring systems may include one or more heteroatoms selected from oxygen, nitrogen or sulfur. The aromatic carbocycle may be optionally substituted by one or more substituents herein described as "substituent X", "substituent A", "substituent B" or "substituent C". When the aromatic carbocycle is a biphenyl, the substituents X, A, B or C may be, independently, on one or both rings. This is similarly so for other aromatic carbocyclic rings or ring systems as defined above. It will be recognized by the skilled artisan that a large number of aromatic carbocycles may be made using the silane linker of this invention, provided that the chemistry used to prepare the aromatic carbocycles is compatible with the aryl silane bond, defined below. Suitable aromatic carbocycles include, but are not limited to, optionally substituted phenyl rings, optionally substituted naphthyl rings, optionally substituted tetrahydronaphthyl rings, optionally substituted anthracenyl rings, optionally substituted 1-, 2- or 3- tetrahydrobenzazepines; optionally substituted 1,4-, 1,5-, or 2,4- tetrahydrobenzodiazepines; optionally substituted biphenyl tetrazoles; optionally substituted 1,3- or 1,4-diaminobenzene compounds; or optionally substituted 1,3- or 1,4-aminocarboxyphenyl compounds. Suitably, the aromatic carbocycles described herein may serve as core structures, and therefore, as templates for designing libraries of compounds to be screened as pharmaceutical agents. Suitably, the aromatic carbocycles are G-protein coupled receptor ligands, channel blockers and/or enzyme inhibitors.

The terms "resin-bound synthesis" and "solid phase synthesis" are used herein interchangeably to mean one or a series of chemical reactions used to prepare either a single compound or a library of molecularly diverse compounds, wherein the chemical reactions are performed on a compound, suitably, an aromatic carbocycle, which is bound to a polymeric resin support through an appropriate linkage, suitably, a silane linker.

The terms "resin," "inert resin," polymeric resin" or "polymeric resin support" are used herein at all occurrences to mean a bead or other solid support such as beads, pellets, disks, capillaries, hollow fibers, needles, solid fibers, cellulose beads, pore-glass beads, silica gels, grafted co-poly beads, poly-acrylamide beads, latex beads, dimethylacrylamide beads optionally cross-linked with N,N'-bisacryloyl ethylene diamine, glass particles coated with a hydrophobic polymer, etc., i.e., a material having a rigid or semi-rigid surface. The solid support is suitably made of, for example, cross linked polystyrene resin, polyethylene glycol-polystyrene resin, and any other substance which may be used as such and which would be known or obvious to one of ordinary skill in the art. For purposes herein, it will be obvious to the skilled artisan, that since the linker to the resin is silicon-based, the above terms mean any aliphatic or aromatic polymer which lacks functionality known to participate in the additional synthetic chemistry used for derivatizing the compound prepared by solid phase synthesis, and which is stable to conditions for protodesilylation. Preferred polymer resins for use herein are the Benzhydrylamine resin (available commercially) and the Aminomethylpolystyrene resin (available commercially). It should be recognized that the resin which is eventually coupled to the aryl silane intermediate, defined infra, should comprise a pendant amino functionality.

The terms "silane linker" or "silane linker group" are used herein at all occurrences to mean the moiety which binds the aromatic carbocycle to the polymeric resin support, which linker comprises a silicon atom bound to an alkyl chain comprising one or more methylene groups, said alkyl chain having a terminal carbonyl moiety. A suitable silane linker for use in this invention comprises a moiety of the following formula —C(O)—(CH$_2$)$_n$-SiR$^a$R$^b$, wherein R$^a$ and R$^b$ are independently, C$_1$ to C$_6$ alkyl and n is an integer from 2 to 20. Preferably, R$^a$ and R$^b$ are independently, C$_1$ to C$_4$ alkyl, more preferably, R$^a$ and R$^b$ are both methyl or ethyl, more preferably methyl. Preferably n is 3.

The term "aryl silane compound" is used herein at all occurrences to mean an intermediate compound comprising an aromatic carbocycle having an aromatic carbon and at least one substituent X, A, B or C that is not hydrogen or alkyl, wherein the aromatic carbon is bound to a silane linker through an aryl silane bond.

The term "aryl silane bond" is used herein at all occurrences to mean the bond between the aromatic carbon of an aromatic carbocycle and the silicon atom of a silane linker. Suitably, after the resin-bound synthesis is performed, this bond is cleaved by acid catalyzed protodesilylation in order to decouple the aromatic carbocycle from the resin-bound aryl silane intermediate.

The term "resin-bound aryl silane intermediate" is used herein at all occurrences to mean an intermediate wherein an aromatic carbocycle is directly bound to a silane linker, which linker is directly bound to a polymeric resin support. Therefore, it will be recognized that a resin-bound aryl silane intermediate is a moiety which couples an aromatic carbocycle to a polymeric resin support through a silane linker. See, for example, Formula (I) infra.

The terms "substituent X," "substituent A," "substituent B," and "substituent C" are used herein at all occurrences to mean a non-nucleophilic substituent, including, but not limited to, hydrogen, halogen, alkyl, alkenyl, alkynyl, alkoxy, aryloxy, thioether (e.g., -alkyl-S-alkyl-), alkylthio (e.g., alkyl-SH), C(O)R$^a$, wherein R$^a$ is hydrogen or alkyl, t-butoxyamino-carbonyl, cyano, nitro (—NO$_2$), aryl, heteroaryl, arylalkyl, alkyl disulfide (e.g., alkyl-S-S-), aryl disulfide (e.g., aryl-S-S-), acetal (alkyl(O-alkyl)$_2$), thioacetal (alkyl(S-alkyl)$_2$), fluorenylmethoxycarbonyl or orthoester (—C(OR)$_3$, wherein R is C$_1$ to C$_4$ alkyl). The substituents X, A, B and C are chosen independently from one another. In addition, X, A, B and C can not all be hydrogen and X, A, B and C can not all be alkyl. When the aromatic carbocycle is a biphenyl, the substituents X, A, B or C may be, independently, on one or both rings. This is similarly so for other aromatic carbocyclic rings or ring systems as defined above. As used herein, modification of the substituents produces a derivatized aromatic carbocycle. The nature of the substituents X, A, B and C, must be compatible with the reaction conditions used for modifying said substituents without said conditions being capable of cleaving the aryl silane bond of the resin-bound aryl silane intermediate. Therefore, it will be recognized that when modification of substituents X, A, B or C by performing additional synthetic chemistry thereon utilizes reaction conditions such that the aryl silane bond is subject to cleavage, it is desirable to choose a strong electron withdrawing group as the substituent(s). Additional synthetic chemistry can then be performed to modify the substituent(s) without cleavage of the aryl silane bond. Subsequent to performing the additional synthetic chemistry to modify the substituent(s), it is possible to cleave the aryl silane bond which decouples the aromatic carbocycle from the resin-bound aryl silane intermediate. If desired, synthetic chemistry conventional in the art may then be performed on the cleaved derivatized aromatic carbocycle to convert the strong electron withdrawing group into a different functionality, e.g., conversion of a nitro group into an amino group using known reaction conditions. Given this disclosure, the types of synthetic chemistry which are compatible with the goal of derivatizing the resin-bound aromatic carbocycle, without also cleaving the aryl silane bond of the resin-bound aryl silane intermediate, will be obvious to one of ordinary skill in the art.

The term "additional synthetic chemistry" is used herein at all occurrences to mean one or a series of chemical reactions which are performed on the resin-bound aryl silane intermediate, in particular to modify or derivatize substituents X, A, B and C, prior to cleavage of the aromatic carbocycle from the resin-bound aryl silane intermediate, wherein said chemical reactions are compatible with and non-reactive with the aryl silane bond, especially silicon in the presence of an amide, and may be used to prepare derivatives of the aromatic carbocycle. It will be recognized by the skilled artisan that the additional synthetic chemistry performed on the resin-bound aryl silane intermediate is done so prior to cleavage of the aryl silane bond. Chemical reactions which are compatible with the resin-bound aryl silane intermediate, are reactions which effectuate the swelling of the polymeric resin thereby allowing penetration of the reagents to react with the aromatic carbocycle. Chemical reactions which are reactive with the aryl silane bond, i.e., they cause cleavage of the aryl silane bond, and therefore are not among the additional synthetic chemistry that may be used in the methods of this invention, are for example, chemical reactions which use strongly acidic conditions or strong electrophilic oxidizing agents (e.g., benzoyl peroxide under acidic conditions).

The term "G-protein coupled receptor(s)" is used herein at all occurrences to mean a 7-transmembrane receptor using G-proteins as part of their signaling mechanism, including, but not limited to muscarinic acetylcholine receptors, adenosine receptors, adrenergic receptors, IL-8R receptors, dopamine receptors, endothelin receptors, histamine receptors, calcitonin receptors, angiotensin receptors and the like.

The term "assay" is used herein at all occurrences to mean a binding assay or a functional assay known or obvious to one of ordinary skill in the art, including, but not limited to, the assays disclosed herein The term "alkyl" is used herein at all occurrences to mean a straight or branched chain radical of 1 to 20 carbon atoms, unless the chain length is limited thereto, including, but not limited to methyl, ethyl, n-propyl, isopropyl, n-butyl, sec-butyl, isobutyl, tert-butyl, and the like. Preferably the alkyl chain is 1 to 10 carbon atoms in length, more preferably 1 to 8 carbon atoms in length.

The term "alkenyl" is used herein at all occurrences to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length.

The term "alkynyl" is used herein at all occurrences to mean a straight or branched chain radical of 2–20 carbon atoms, unless the chain length is limited thereto, wherein there is at least one triple bond between two of the carbon atoms in the chain, including, but not limited to, acetylene, 1- propylene, 2-propylene, and the like. Preferably, the alkynyl chain is 2 to 10 carbon atoms in length, more preferably, 2 to 8 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein at all occurrences to mean a straight or branched chain radical of 1 to 20 carbon atoms, unless the chain length is limited thereto, bonded to an oxygen atom, including, but not limited to, methoxy, ethoxy, n- propoxy, isopropoxy, and the like. Preferably the alkoxy chain is 1 to 10 carbon atoms in length, more preferably 1 to 8 carbon atoms in length.

The terms "cycloalkyl" and "cyclic alkyl" are used herein at all occurrences to mean cyclic radicals, preferably comprising 3 to 10 carbon atoms which may be mono- or bicyclo- fused ring systems which may additionally include unsaturation, including, but not limited to, cyclopropyl, cyclopentyl, cyclohexyl, 1,2,3,4-tetrahydronaphthyl, and the like.

The terms "aryl" or "heteroaryl" are used herein at all occurrences to mean 5–14 membered optionally substituted aromatic ring(s) or ring systems which may include bi- or tri-cyclic systems and one or more heteroatoms, wherein the heteroatoms are selected from oxygen, nitrogen or sulfur. Representative examples include, but are not limited to, phenyl, naphthyl, pyridyl, quinolinyl, thiazinyl, isoquinoline, imidazole, 3,4-dimethoxyphenyl, 3,4-methylenedioxyphenyl, 3,4-dimethoxybenzyl, 3,4-methylenedioxy-benzyl, benzhydryl, 1-naphthylmethyl, 2-naphthylmethyl, fluorenyl, biphenyl-4-methyl, furanyl, and the like.

The term "heteroatom" is used herein at all occurrences to mean an oxygen atom ("O"), a sulfur atom ("S") or a nitrogen atom ("N"). It will be recognized that when the heteroatom is nitrogen, it may form an $NR^1R^2$ moiety, wherein $R^1$ and $R^2$ are, independently from one another, hydrogen or $C_1$ to $C_8$ alkyl, or together with the nitrogen to which they are bound, form a saturated or unsaturated 5-, 6-, or 7-membered ring.

The terms "arylalkyl" and "heteroarylalkyl" are used herein at all occurrences to mean an aryl or heteroaryl moiety, respectively, that is connected to a $C_{1-8}$ alkyl moiety as defined above, such as, but not limited to, benzyl.

The term "5- 6-, or 7-membered ring" is used herein at all occurrences to mean that substituents $R^1$ and $R^2$, together with the nitrogen to which they are bound, form a saturated or unsaturated ring structure containing at least one additional heteroatom selected from oxygen, nitrogen or sulfur, including, but not limited to morpholine, piperazine, piperidine, pyrolidine, pyridine, and the like.

The term "heterocyclic" is used herein at all occurrences to mean a saturated or wholly or partially unsaturated 4–10 membered ring system in which one or more rings contain one or more heteroatoms selected from the group consisting of O, N, or S; including, but not limited to, pyrrolidine, piperidine, piperazine, morpholine, imidazolidine, pyrazolidine, benzodiazepines, and the like.

The term "halogen" is used herein at all occurrences to mean chloro, fluoro, iodo and bromo.

The term "Ph" is used herein at all occurrences to mean phenyl.

The term "optionally substituted" is used herein at all occurrences to mean that the optionally substituted moieties may or may not be substituted with one to three various functional groups including, alkyl, alkenyl, alkynyl, aryl, cycloalkyl, heteroaryl, heterocyclo groups arylalkyl, heteroarylalkyl, halogen, cyano, —$(CR^{11}R^{12})_n$-C(O)R'''; —$(CR^{11}R^{12})_n$-NO$_2$; —$(CR^{11}R^{12})_n$-OR'; $(CR^{11}R^{12})_n$-SR'''; —$(CR^{11}R^{12})_n$-N(R')$_2$; —$(CR^{11}R^{12})_n$-NHC(O)R'''; —$(CR^{11}R^{12})_n$-CO$_2$R'''; —$(CR^{11}R^{12})_n$-CON(R''')$_2$; —$(CR^{11}R^{12})_a$(C=C)$_b$$(CR^{11}R^{12})_c$Z, or $(CR^{11}R^{12})_a$(C=C)$_b$W$(CR^{11}R^{12})_c$Z'; wherein Z' is C(O)R', CO$_2$R''', NO$_2$; OR'''; S R'''; N(R''')$_2$, NHC(O)R'''; or CON (R''')$_2$; a is 0 or 1, b is 0 to 10 and c is 0 to 10, preferably a=b=c is less than 10; W' is N or S; R''' is hydrogen, (C$_1$–C$_4$) alkyl, aryl, arylalkyl, or heteroaryl; and R$^1$ and R$^{12}$ are independently hydrogen or a branched or straight chain C$_1$ to C$_6$ alkyl, alkenyl or alkynyl; and, for purposes herein, n is 0 or is an integer from 1 to 10. It is recognized that these substituents may be further substituted by groups similar to those indicated above herein to give substituents such as halo-substituted alkyl (e.g., —CF$_3$), aryl-substituted alkyl, alkoxy-substituted alkyl and the like. For example, in the term $(CR^{11}R^{12})_n$-N(R''')$_2$, n is 1, R$^{11}$ is —CH$_2$CH=CH$_2$, R$^{12}$ is hydrogen, one of R''' is hydrogen and one of R''' is benzyl; in the term —$(CR^{11}R^{12})_n$SR''', n is 1, R''' is phenyl, R$^{12}$ is hydrogen, R$^{11}$ is a substituted alkyl, specifically a methyl substituted by —COOR''' and R''' is hydrogen, methyl or ethyl; in the term alkenyl, the alkenyl moiety may be substituted by —$(CR^{11}R^{12})_n$-C(O)R''' or —$(CR^{11}R^{12})_n$-CO$_2$R''', wherein R''' is hydrogen, methyl or ethyl; in the term $(CR^{11}R^{12})_a$(C=C)$_b$$(CR^{11}R^{12})_c$Z', a is 1, b is 1, c is 0, Z' is NR''', R$^{11}$ and R$^{12}$ are H and R''' is benzyl; in the term $(CR^{11}R^{12})_a$(C=C)$_b$W'$(CR^{11}R^{12})_c$Z', W' is N and a is 1, b is 1, c is 0, Z' is NR''', R$^{11}$ and R$^{12}$ are H and R''' is benzyl.

Preferred optional substituents for use herein include alkyl, alkenyl, alkoxy, cyano, NO$_2$, halogen, preferably bromine, —$(CR^{11}R^{12})_n$C(O)R''', —$(CR^{11}R^{12})_n$-SR''', —$(CR^{11}R^{12})_n$-N(R''')$_2$ and aryl, preferably phenyl. More preferably, the optional substituents are C$_1$ to C$_{10}$ alkyl, C$_1$ to C$_{10}$ alkoxy, cyano, C(O)R''', NO$_2$, halogen, and aryl.

In contrast to the resins and linkers known in the art, the instant polymeric resins and silane linkers are particularly useful in effectuating the cleavage of an aromatic carbocycle from a polymeric resin support while leaving a hydrogen at the cleavage position.

In one aspect, the invention is in a method for preparing a compound by resin-bound synthesis, wherein said compound is an aromatic carbocycle comprising an aromatic carbon atom and at least one substituent that is not hydrogen or alkyl, said method comprising the steps of: (i) attaching the aromatic carbon to a polymeric resin support through a silane linker to give a resin-bound aryl silane intermediate; and (ii) performing additional synthetic chemistry on the substituent so that the aromatic carbocycle is derivatized. The derivatized resin-bound aryl silane intermediate may be stored for further derivatization of the substituents. Suitably, the aromatic carbocycle is biphenyl, phenyl, naphthyl or anthracenyl. Suitably, the aromatic carbocycle has at least one substituent that is X, A, B or C, as defined above, to be derivatized by additional synthetic chemistry. A compound prepared by this method remains as a resin-bound aryl silane intermediate, which resin-bound intermediate may be screened in a suitable assay developed for determining pharmaceutical activity.

Alternatively, the derivatized aromatic carbocycle may be decoupled from the resin-bound aryl silane intermediate by a further step comprising cleaving the resin-bound aryl silane intermediate at the aryl silane bond so that the decoupled aromatic carbocycle resulting from the cleavage has a hydrogen on the aromatic carbon where it was bound through the silane linker. After this step, the decoupled aromatic carbocycle may be screened in a suitable assay developed for determining pharmaceutical activity.

As described above, the additional synthetic chemistry performed in order to modify the substituents X, A, B or C must be such that the aromatic carbocycle is derivatized without cleaving the aryl silane bond of the resin-bound aryl silane intermediate.

According to this invention, the aromatic carbocycle is bound to a polymeric resin support through the improved silyl linker to give a resin-bound aryl silane intermediate. In particular, the aromatic carbocycle is bound to the resin through a silane linker group comprising the following moiety: C(O)—(CH$_2$)$_n$-Si-R$^a$R$^b$, wherein R$^a$ and R$^b$ are independently, C$_1$ to C$_6$ alkyl and n is an integer from 2 to 20. For purposes herein, the aromatic carbon atom of the aromatic carbocycle is bound directly to a silicon atom of the silane linker. Preferably, R$^a$ and R$^b$ are independently, C$_1$ to C$_4$ alkyl, more preferably, R$^a$ and R$^b$ are both methyl or ethyl, more preferably R$^a$ and R$^b$ are both methyl. Preferably n is the integer 3.

Useful intermediates of the invention are the resin-bound aryl silane intermediates of Formula (I). The compounds of Formula (I) are further modified by performing additional synthetic chemistry thereon. Preferably, an aryl silane compound is formed as a first intermediate, which intermediate is then coupled (using conventional techniques) to a polymeric resin support such as benzhydrylamine resin, to give a compound of Formula (I):

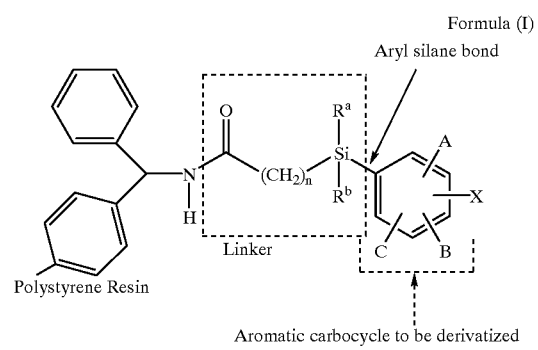

Formula (I)

wherein R$^a$ and R$^b$, independently from one another, are C$_1$ to C$_6$ alkyl; X, A, B and C are, independently from one another, hydrogen, halogen, alkyl, alkenyl, alkynyl, alkoxy, alkylthio, C(O)R$^d$, wherein R$^d$ is hydrogen or alkyl, t-butoxyaminocarbonyl, cyano, nitro, aryl, heteroaryl, arylalkyl, alkyl disulfide, aryl disulfide, acetal, fluorenylmethoxycarbonyl or orthoester group, provided that X, A, B and C can not all be hydrogen and X, A, B and C can not all be alkyl; and n is an integer from 2 to 20.

In all cases, after the aromatic carbocycle portion of the resin-bound aryl silane intermediate is modified by the additional synthetic chemistry, the derivatized aromatic carbocycle may be cleaved from the resin-bound aryl silane intermediate at the aryl silane bond or it may remain as a resin-bound aryl silane intermediate. Neat TFA or TFA vapor are the most preferred reagents to effectuate cleavage of the aryl silane bond.

In yet another aspect, this invention is in a method for preparing a library of diverse resin-bound aromatic carbocycles each comprising an aromatic carbon atom and at least one substituent that is not hydrogen or alkyl, said method comprising the steps of: (i) attaching the aromatic carbon atom of each of a plurality of aromatic carbocycles to an individual polymeric resin support through a silane linker to give a plurality of resin-bound aryl silane intermediates; (ii) optionally dividing said resin-bound aryl silane intermediates into a plurality of portions; (iii) performing additional synthetic chemistry on the substituents so that the aromatic carbocycle is derivatized; and (iv) optionally recombining the portions. Suitably, the substituents on the aromatic carbocycle which are to be derivatized are X, A, B or C as defined above.

For example, a plurality of aromatic carbocycles each comprising an aromatic carbon atom and having at least one substituent X, A, B or C that is not hydrogen or alkyl, are each attached to an individual polymer resin support through a silane linker to give a plurality of resin-bound aryl silane intermediates. In a first step modification to the substituent (s) on the aromatic carbocycle, the plurality of resin-bound aryl silane intermediates may be reacted with one or more reagents in one reaction vessel. Alternatively in a first step modification, aliquots of the resin-bound aryl silane intermediates may be reacted with one or more reagents and then the resultant products are mixed together to form a library of derivatized aromatic carbocycles. Preferably, the reagent(s) used in this first step modification will modify only a single substituent X, A, B or C.

This first modified/derivatized library may then be further derivatized by repeating the process of dividing and recombining the derivatized resin-bound aryl silane intermediates formed by the additional synthetic chemistry. It will be obvious to the skilled artisan that the resin-bound aryl silane intermediates may be divided into portions at any point during the synthetic scheme. The portions may be recombined at any point during the scheme or, further iterations may be applied if more derivatization is required. For example, after a first step modification where the aliquots were divided and reacted with one or more appropriate reagents, the derivatized aliquots may be recombined and reacted with one or more additional reagents in one reaction vessel. Alternatively, each aliquot may be subdivided into further aliquots and reacted as described herein.

Therefore, it will be obvious to the skilled artisan that the steps of dividing the portions, performing additional synthetic chemistry and recombining the portions, may each be carried out more than once. The steps of optionally dividing and recombining the resin-bound aryl silane intermediates into portions are for purposes of varying the derivatization, depending upon the type of diversity required for the library of end-product aromatic carbocycles being prepared by the combinatorial synthesis. Suitably, when the libraries of the invention are prepared according to the instant disclosure, each polymeric resin support bears a single (derivatized) aromatic carbocycle species created by the additional synthetic chemistry performed on the resin-bound aryl silane intermediate.

The instant silyl linker was developed as an improvement over known silyl linkers for use in solid phase combinatorial or multiple simultaneous synthesis. As described above, the inventors were interested in the solid phase synthesis of molecules of the general structure represented by 4-Scheme 1, and the use of an aryl silane linker as disclosed in WO 95/16712 (see dotted box in structure 2 above at page 2) provided an attractive synthetic route as shown in Scheme 1. The design of resin-bound aryl silane intermediate 2, shown above at page 2, which is attached to Merrifield resin via an ether linkage, was modified in order to introduce a carboxylic acid functionality which could be coupled to benzhydrylamine (BHA) resin to give resin-bound aryl silane intermediate 3, shown above at page 2. Modifying the linker portion of 2 was thought to afford several advantages. First, intermediate carboxylic acid 1-Scheme 1, could be prepared in solution and rigorously purified and characterized before attachment to the resin to form the resin-bound aryl silane intermediate. Attachment to the BHA resin would be via an amide bond formation reaction, a highly optimized solid phase reaction which allows for monitoring the extent of attachment of material to resin by the ninhydrin test (Kaiser, et al., *Anal. Biochem.* 1970, 34, 594–598) and then driven to completion. The resulting resin construct was expected to be both homogeneous and of known loading, both of which facilitate analysis of the subsequent synthetic reactions performed.

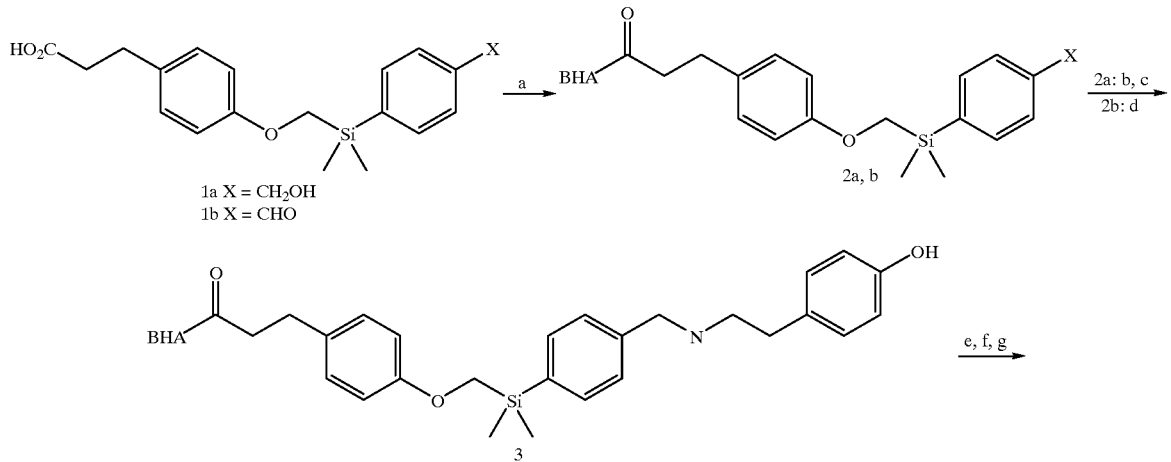

-continued

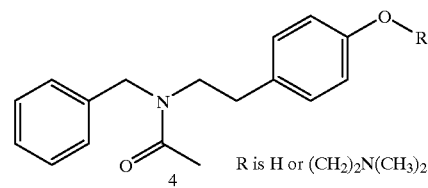

R is H or (CH$_2$)$_2$N(CH$_3$)$_2$

[a] Reagents: (a) benzhydrylamine resin, DCC, HOBt, DMF; (b) CBr$_4$, Ph$_3$P, THF; (c) tyramine, Et$_3$N;
(d) tyramine, NaBH$_3$CN, MeOH, AcOH; (e) ROH, Ph$_3$P, DIAD, THF; (f) MeCO$_2$H, DCC, HOBt; (g) TFA.

However, during initial synthetic experiments, unexpected difficulties were encountered in isolating the expected intermediates after neat TFA cleavage from the resin. In fact, neither benzyl alcohol from cleavage of 2a-Scheme 1 nor benzaldehyde from cleavage of 2b-Scheme 1 were able to be isolated. An investigation of the cleavage chemistry indicated that an unexpected alternative cleavage pathway was occurring when resin-bound aryl silane intermediate 3 (see structure on page 2) was used as in Scheme 1. Because of this unexpected result, the linker portion of intermediate 3 (see dotted box on intermediate at page 2 supra) was modified to give a novel linker as depicted in the dotted box area of resin-bound aryl silane intermediate 4 (page 2 supra). Using this novel linker, all the requisite chemistry shown in Scheme I was successfully demonstrated.

Before developing the improved silyl-linker of this invention, a linker modeled after the silyl linkers disclosed in WO 95/16712 (structure 3, supra) was proposed for synthesizing compound 8-Scheme 2. 4-Bromobenzyl alcohol was protected as the triisopropylsilyl ether 2-Scheme 2, which was then converted to the Grignard reagent and reacted with (bromomethyl)-chlorodimethylsilane to give the bromomethylsilane 3-Scheme 2. Treatment of 3-Scheme 2 with methyl 3-(4-hydroxyphenyl)propionate and potassium carbonate in refluxing 2-butanone gave the silylmethyl phenyl ether 4-Scheme 2, which was deprotected to give the benzyl alcohol 5-Scheme 2. Oxidation of 5-Scheme 2 with manganese dioxide to the aldehyde 6-Scheme 2 followed by reductive amination with tyramine and acetylation with acetic anhydride gave the desired model compound 8-Scheme 2.

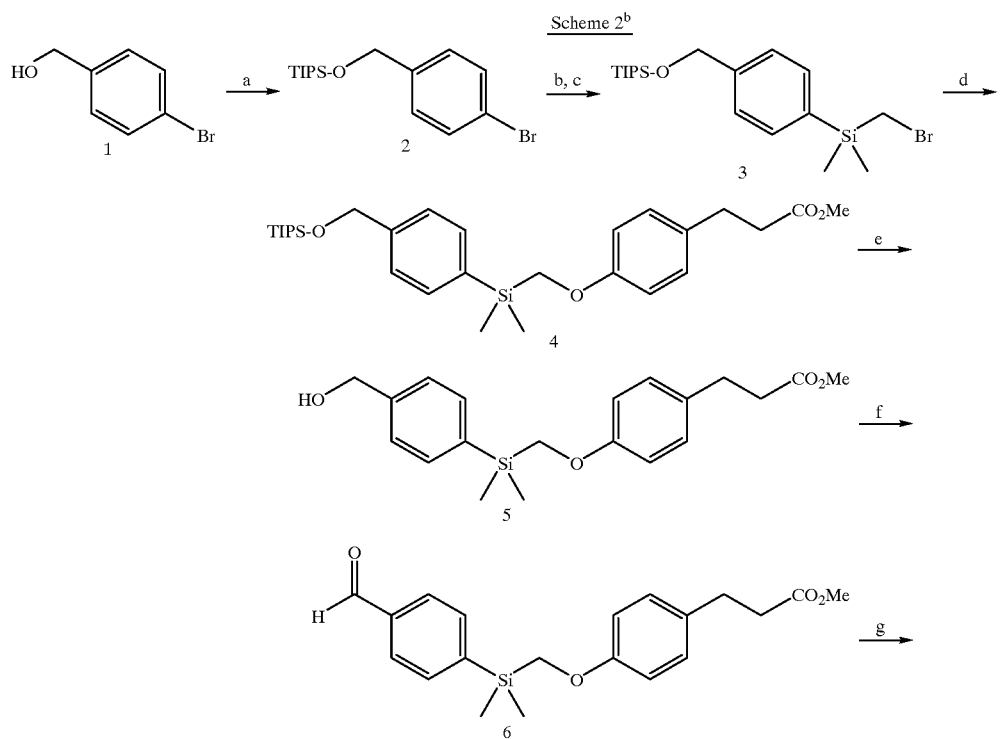

-continued

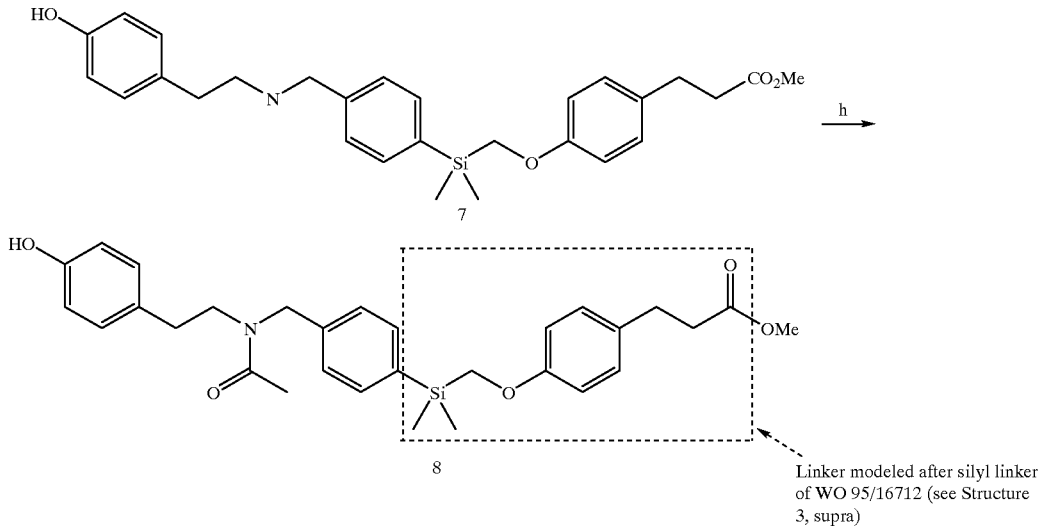

Linker modeled after silyl linker of WO 95/16712 (see Structure 3, supra)

[b] Reagents: (a) TIPS-Cl, imidazole, DMF; (b) Mg, THF; (c) ClSi(CH$_3$)$_2$Br; (d) methyl 3-(4-hydroxyphenyl)propionate, K$_2$CO$_3$, 2-butanone, reflux; (e) HOAc/THF/H$_2$O 3:1:1, 45° C. 24h; (f) MnO$_2$, CH$_2$Cl$_2$, reflux; (g) tyramine, HOAc, NaBH$_3$CN, MeOH; (h) Ac$_2$O, pyridine, CH$_2$Cl$_2$.

Compound 8-Scheme 2 was then subjected to several different cleavage reactions. The results are summarized in Scheme 3. Treatment of 8-Scheme 2 with neat TFA at room temperature did not give the desired compound 3-Scheme 3. The phenol 1-Scheme 3, which arises from an alternative cleavage of the carbon-oxygen bond in the linker, was instead isolated in quantitative yield along with a second product which has been tentatively assigned to the structure 2-Scheme 3 based on $^1$H NMR and mass spectral data. This cleavage pattern and distribution of products has been observed previously in the cleavage of silylmethyl methyl ethers with trimethylsilyl iodide (Cunico, R. F.; Gill, H. S. *Organometallics* 1982, 1, 1–3).

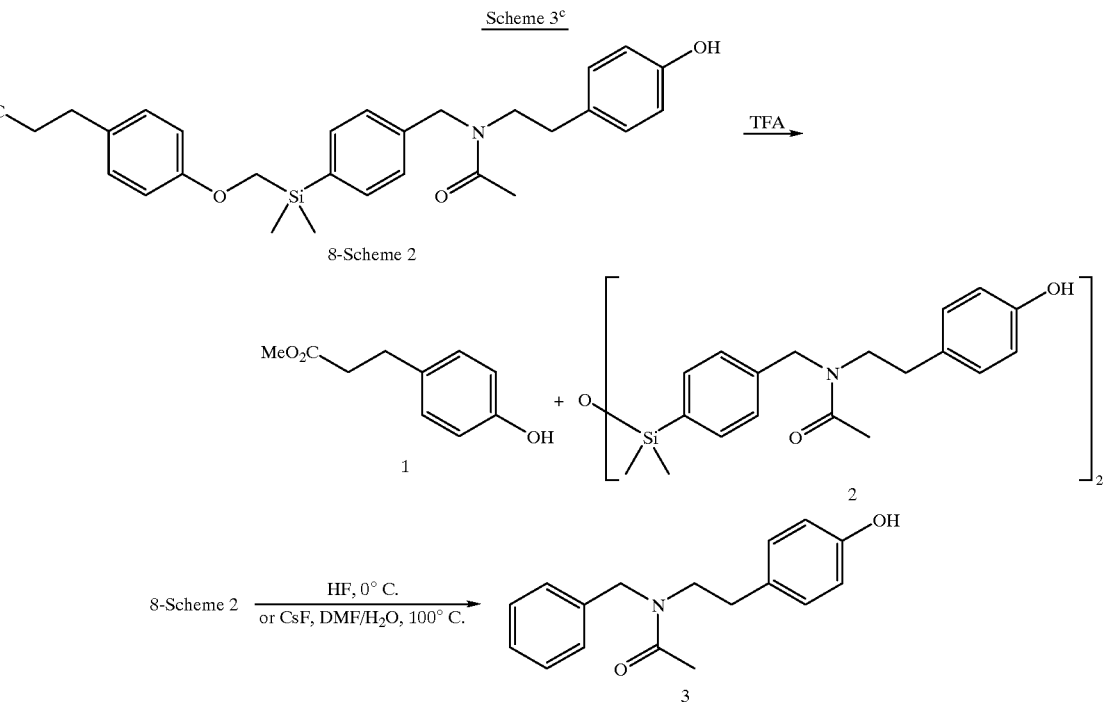

Interestingly, the desired product 3-Scheme 3 was obtained following treatment of 8-Scheme 2 with HF or CsF, although small amounts of 1-Scheme 3 and 2-Scheme 3 were also detected by HPLC analysis of the crude cleavage reaction mixture. These conditions, however, are less attractive from the point of view of combinatorial or simultaneous multiple synthesis. HF can be difficult to handle and requires a relatively complex apparatus. After CsF cleavage, the compound is obtained as a mixture containing any excess CsF along with other cesium salts in a relatively non-volatile solvent. The effective use of combinatorial or multiple simultaneous synthesis requires that the cleavage chemistry leave the minimum amount of extraneous residue behind and that the workup be minimal, preferably just evaporation of a volatile cleavage reagent. The instant silyl linker solves such synthetic problems and allows for cleavage of the resin-bound aryl silane intermediate with neat TFA.

In solution, compound intermediate 5-Scheme 4 was readily prepared according to Scheme 4. The benzyl alcohol silyl propionate 2-Scheme 4 was prepared from the corresponding 4-bromobenzyl alcohol in six steps. Treatment of 3-Scheme 2 with the sodium salt of dimethyl malonate gave 1-Scheme 4, which was deprotected to the benzyl alcohol and then demethoxycarbonylated with lithium chloride in DMSO and water to give 2-Scheme 4. Oxidation to the benzaldehyde 3-Scheme 4 with $MnO_2$, reductive amination with tyramine and acetylation of the secondary amine with acetic anhydride gave the silyl linked compound 5-Scheme 4. Treatment of 5-Scheme 4 with neat TFA produced the desired product compound 3-Scheme 3 with no evidences of any side reactions.

Application of the improved silyl linker to solid phase chemistry was shown to be effective by preparing 3-Scheme 3 as shown in Scheme 5. 5-Scheme 4 was saponified and the resulting free acid 1-Scheme 5 was coupled to BHA resin to give 2-Scheme 5. Treatment of 2-Scheme 5 with neat TFA for 40 h at room temperature gave a quantitative yield of 3-Scheme 3. As is often the case with solid phase cleavage reactions, the crude product was quite clean, with no detectable impurities or contamination by starting material.

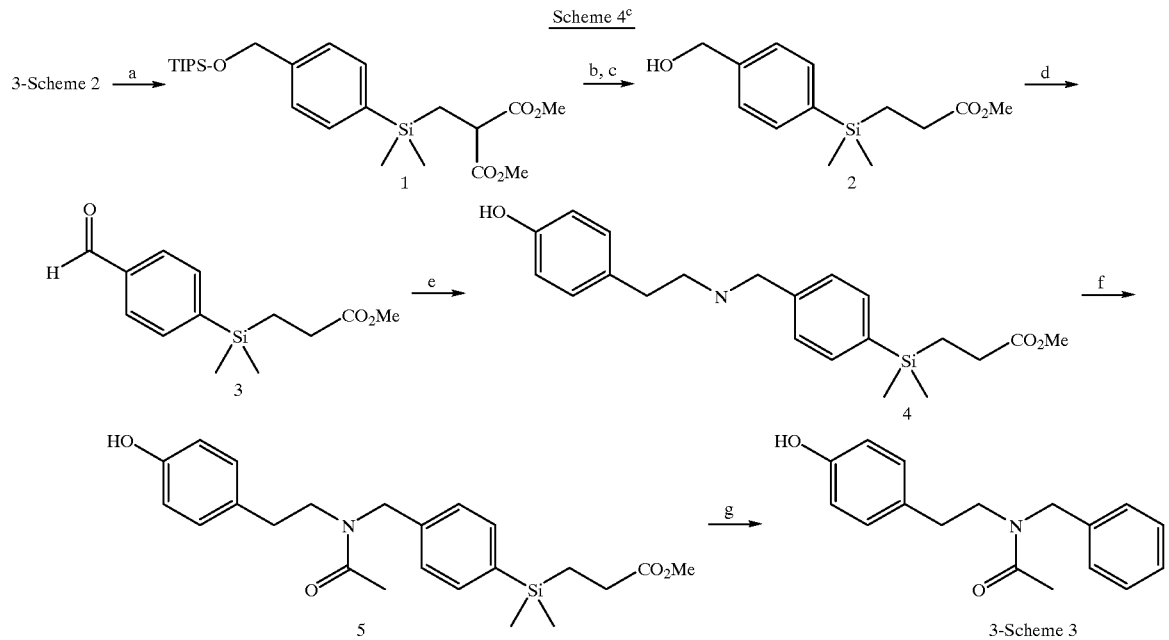

Scheme 4$^c$ $^c$ Reagents: (a) dimethylmalonate, NaOMe, MeOH; (b) HOAc, $H_2O$, THF; (c) LiCl, $H_2O$, DMSO, 140° C. 24h; (d) $MnO_2$, $CH_2Cl_2$, reflux; (e) tyramine, $NaBH_3CN$, HOAc, MeOH; (f) $Ac_2O$, pyridine; (g) TFA.

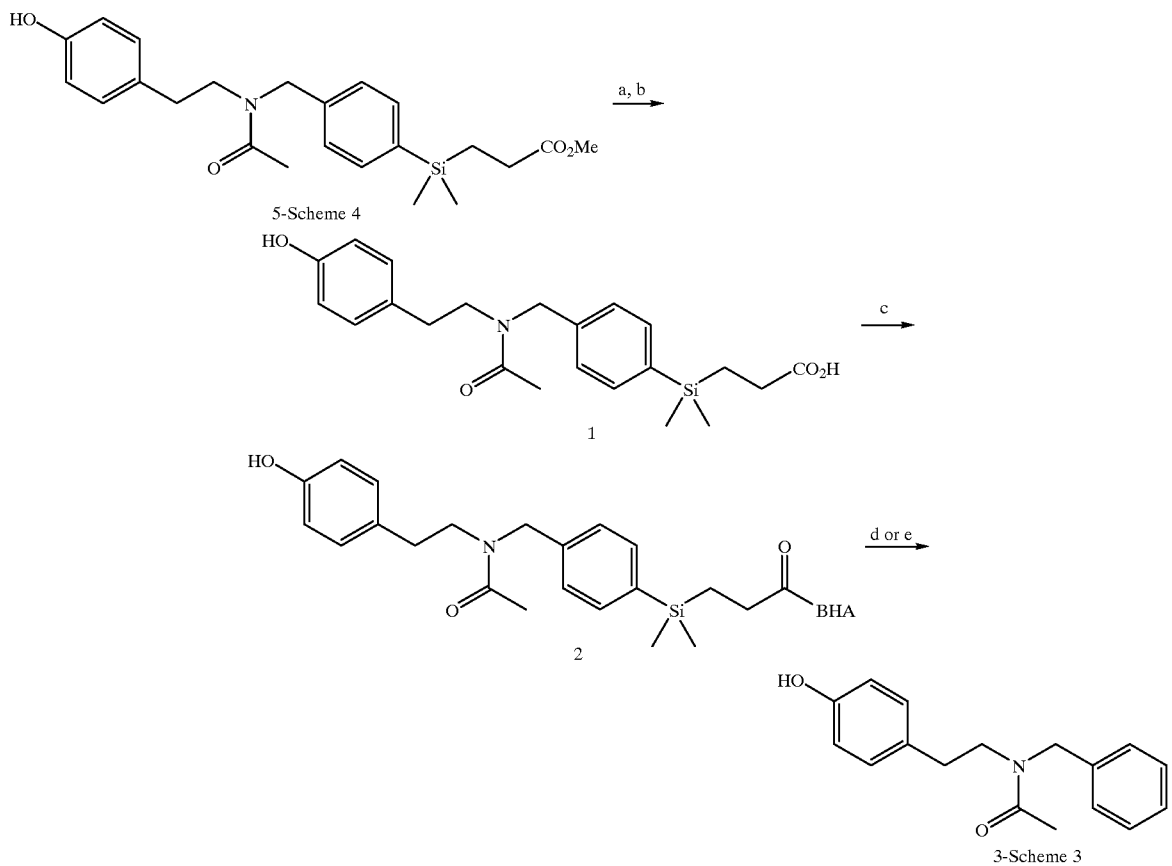

Scheme 5[d]

[d] Reagents: (a) NaOH, H₂O, dioxane; (b) HCl; (c) BHA, DCC, HOBt, DMF; (d) TFA (neat); (e) TFA (vapor).

In addition to neat TFA, TFA vapor has also been used to cleave compounds from acid-labile resins (Jayawickreme et al., *Proc. Natl. Acad. Sci. USA* 1994, 91, 1614–1618). The use of TFA vapor affords some advantages in combinatorial or multiple synthetic strategies. With liquid TFA (either neat or containing scavengers), the compound is cleaved off the resin and extracted into the TFA solution. This necessitates the filtering and handling of a hazardous, corrosive and volatile material. After cleavage with TFA vapor, however, the compounds remain adsorbed to the resin and are eluted with a solvent which is both less dangerous to handle and more suitable for biological screening. The apparatus required is quite simple. Beads are distributed into small sintered glass funnels or 96-well filter plates, which are suspended in a TLC chamber or desiccator containing a small volume of TFA at the bottom. After the desired reaction time, the funnels or plates are simply removed and placed in a vacuum desiccator to remove residual TFA. The beads can then be extracted and eluted with a solvent such as methanol, acetic acid, or dimethylformamide.

An experiment supporting the kinetics of cleavage of the compound off the resin was conducted by exposure of the resin-bound aryl silane intermediate 2-Scheme 5 to a single exposure to TFA. The time course of vapor phase TFA cleavage of 2-Scheme 5 is shown in FIG. 1. Weighed aliquots of 2-Scheme 5 were cleaved for various times, extracted with 2% MeOH in CHCl₃ and the amount of 3-Scheme 3 obtained was quantitated by HPLC. The time course for vapor phase cleavage is quite similar to the solution cleavage results, with a $t_{1/2}$ of about 13 h and nearly quantitative cleavage occurring by 40 h at room temperature.

The time course of cleavage and the relatively substantial amount of cleavage, approximately 30%, which had occurred in the first six hours of reaction suggested that this resin might be useful for controlled partial release of compound from the resin. Partial release is useful in single bead-associated combinatorial screening. See, Jayawickreme et al., *Proc. Natl. Acad. Sci. USA* 1994, 91, 1614–1618 and Salmon et al., *Proc. Natl. Acad. Sci. USA* 1993, 90, 11708–11712. A portion of the compound can be released from a single bead, eluted and assayed as soluble material. Sufficient compound remains on the bead for subsequent identification. (See, Zambias et al., *Tet. Lett.* 1994, 35, 4283–4286 and Krebs et al., *Biochem.* 1995, 34, 720–723). Partial cleavage has been achieved in a rigorous fashion by the simultaneous use of orthogonally cleavable linkers, but it has also been effected by limited exposure of acid-labile linkers to TFA vapor.

It will be recognized that when the instant silyl linker is used in solid phase synthesis, partial cleavage may be achieved. For example, an aliquot of 2-Scheme 5 was subjected to several rounds of treatment with TFA vapor. After each partial cleavage, the released aromatic carbocycle 3-Scheme 3 was eluted from the resin and quantified by HPLC. The results are shown in FIG. 2. Approximately 25% of the available 3-Scheme 3 was released from the resin in each of the first two 6-hour exposures to TFA vapor and an additional 10% was released in the third partial cleavage. These numbers are in good agreement with the time course of cleavage in FIG. 1 and indicate that this linker would perform suitably in a partial release strategy.

Scheme 6 incorporates all the chemistry envisioned in Scheme 1 using the improved silyl linker described herein. Scheme 6 also demonstrates some additional synthetic chemistry within the scope of this invention. The chemistry was monitored by elemental analysis and magic angle spinning proton NMR. The benzyl alcohol aryl silane compound 2-Scheme 4 was saponified, coupled to BHA resin and smoothly converted to the benzyl bromide 3-Scheme 6 with $CBr_4$ and triphenylphosphine. This resin-bound benzyl bromide aryl silane intermediate was then used to alkylate tyramine to produce the secondary amine 4-Scheme 6. This reaction demonstrates the power of solid phase synthesis. In a solution reaction, one would expect to obtain a mixture of mono- and di-alkylated tyramines. Using an excess of tyramine and a resin-bound alkylating agent, dialkylation is effectively suppressed and the desired product is obtained cleanly. Acetylation with acetic anhydride to give 5-Scheme 6 followed by Mistunobu reaction with dimethylaminoethanol using DIAD instead of DEAD to avoid formation of any ethyl ether (Krchnak et al., M. Tet. Lett. 1995, 36, 6193–6196) gave the resin-bound aryl silane intermediate 6-Scheme 6. The final product 7-Scheme 6 was obtained in quantitative yield based on starting resin-bound aryl silane intermediate 2-Scheme 6 after cleavage with TFA vapor.

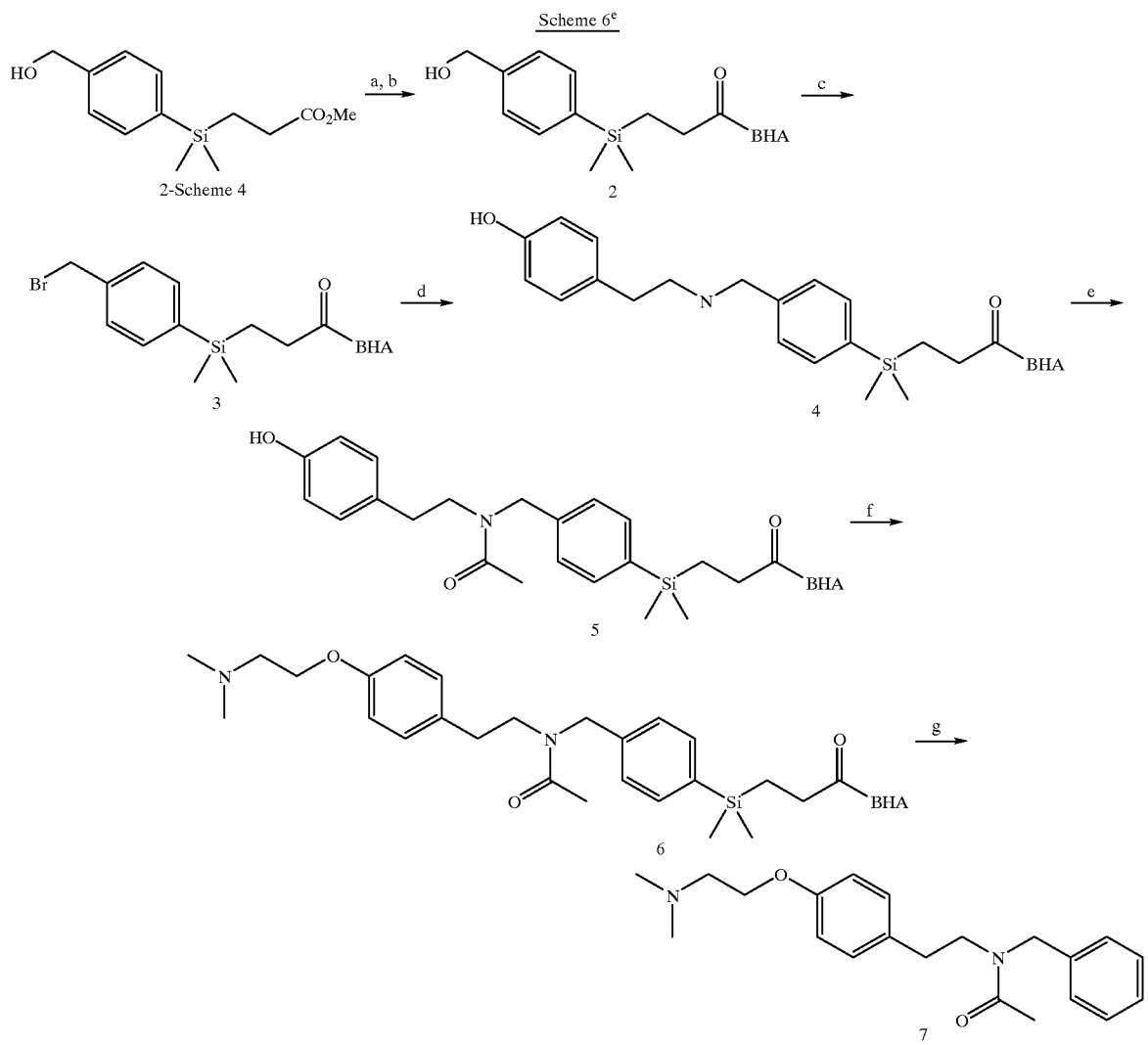

$^e$ Reagents: (a) NaOH, $H_2O$, dioxane; (b) BHA resin, DCC, HOBt, DMF; (c) $CBr_4$, $Ph_3P$, THF; (d) tyramine, $Et_3N$, DMF; (e) $Ac_2O$, pyridine, $CH_2Cl_2$; (f) N,N-dimethylaminoethanol, DIAD, $Ph_3P$, THF; (g) TFA (vapor), RT.

Experimental Section

Abbreviations used herein have the following meanings, unless otherwise stated. Benzhydrylamine resin ("BHA"); Dicyclohexylcarbodiimide ("DCC"); 1-hydroxybenzotriazole hydrate ("HOBt"); Triphenylphosphine ("$Ph_3P$"); diethyl azodicarboxylate ("DEAD"); Diisopropyl azodicarboxylate ("DIAD"); triisopropylsilyl chloride ("TIPS-Cl"); Magic angle spinning ("MAS"); Trifluoroacetic acid ("TFA"); Tetrahydrofuran ("THF"); Triethylamine ("$Et_3N$"); Acetic acid ("AcOH"); Methanol ("MeOH"); and Dimethylsulfoxide ("DMSO"). Reagent grade solvents and commercial reagents were used without additional purification. THF was distilled from sodium ketyl. Proton NMR spectra were obtained at 250 MHz on a Brucker AM 250 spectrometer and at 400 MHz on a Brucker AMX 400 spectrometer. Magic angle spinning proton NMR was obtained on a Varian 500 MHz spectrometer equipped with a magic angle spinning nanoprobe. Chemical shifts are reported relative to tetramethylsilane. Electrospray mass spectra were obtained on a Fisons Instruments VG Biotech spectrometer. Infrared spectra were obtained on a Nicolet Impact 400D Fourier transform infrared spectrophotometer. HPLC was performed on a Beckman System Gold chromatograph.

O-Triisopropylsilyl-4-bromobenzyl alcohol (2-Scheme 2)

To a solution of 4-bromobenzyl alcohol (50.07 g, 268 mmol) in DMF (500 mL) was added with stirring, under Ar, imidazole (40 g, 588 mMol) followed by triisopropylsilyl-chloride (57.3 mL, 268 mMol). After stirring for 24 h at room temperature the reaction was evaporated to dryness, taken up in hexane (500 mL), washed with aq. 1N hydrochloric acid (500 mL), brine (500 mL), dried ($MgSO_4$), and evaporated to give 2-Scheme 2 as a clear oil. (91.72 g, 99%): TLC $r_f$ 0.71 (silica, 50:1 hexane:ethyl acetate); GC rt 2.98 (HP 530µ×20 m methylsilicone column, He carrier flow 20 mL/min., 150° C. init. temp., 10° C./min. rate, 250° C. final temp., 2 min. final time); $^1$H NMR (400 MHz, $CDCl_3$) δ 1.08 (18H, d, J=6.4 Hz), 1.14 (3H, m), 4.78 (2H, s), 7.22 (2H, d, J=8.4 Hz), 7.45 (2H, d, J=8.4 Hz).

[Dimethyl-4-(triisopropylsilyloxymethyl)phenylsilyl]methylbromide (3-Scheme 2)

To a stirred mixture of Mg turnings (2.22 g, 91 mmol) in THF (100 mL) was added 1,2-dibromoethane (300 µL, 3.5 mmol). The mixture was stirred under Ar and heated to 70° C. (reflux). After 5 min. the reaction was cooled to room temperature and a solution of 2-Scheme 2 (30 g, 87.4 mMol) in THF (100 mL) was added in one portion. The reaction was then slowly heated to reflux (slightly exothermic) and allowed to stir for another 5 h until all the Mg was consumed. The resultant pale brown solution was then cooled to −78° C. and a solution of (bromomethyl) chlorodimethylsilane (15 mL, 110 mL) in THF (50 mL) was added slowly over 5 minutes. After stirring for 1 h the reaction was allowed to warm to room temperature and stirred for an additional 16 h. The reaction was evaporated to dryness, taken up in hexane (500 mL), washed with cold aq. 1N hydrochloric acid (500 mL), brine (500 mL), dried ($MgSO_4$) and evaporated. Purification by Kugelrohr distillation (140–150° C.) gave 3-Scheme 2 as a clear oil. (23.54 g, 65%): TLC $r_f$ 0.53 (silica, 50:1 hexane:ethyl acetate); GC rt 8.27 (HP 530-20 m methylsilicone column, He carrier flow 20 mL/min., 150° C. init. temp., 10° C./min. rate, 250° C. final temp., 2 min. final time); $^1$H NMR (400 MHz, $CDCl_3$) δ 0.43 (6H, s), 1.12 (18H, d, J=6.6 Hz), 1.18 (3H, m), 2.63 (2H, s), 7.38 (2H, d, J=8.0 Hz), 7.51 (2H, d, J=8.0 Hz).

Methyl 3-[[dimethyl-4-(triisopropylsilyloxymethyl)phenylsilyl]methyloxy-phenyl]propionate (4-Scheme 2)

To a stirred solution of 3-Scheme 2 (29.57 g, 71 mmol) and methyl 3-(4-hydroxyphenyl)-propionate (12.80 g, 71 mMol) in 2-butanone (200 mL) was added $K_2CO_3$ (9.8 g, 71 mMol). The suspension was stirred under Ar at reflux (80° C.) for 72 h, cooled to room temperature and evaporated to dryness. The residue was taken up in ethyl acetate (500 mL) and washed with aq. 1N HCl (500 mL), brine (500 mL), dried ($MgSO_4$) and evaporated to dryness. Purification by flash chromatography (silica. 5% ethyl acetate/hexane) gave 4-Scheme 2 (22.06 g, 60%) as a clear oil along with recovered starting material. (10.43 g, 35%): TLC $r_f$ 0.49 (silica 10% ethyl acetate/hexane); $^1$H NMR (400 MHz, $CDCl_3$) δ 0.41 (6H,s), 1.09 (18H, d, J=6.5 Hz), 1.17 (3H, m), 2.58 (2H, t), 2.88 (2H, t), 3.66 (3H, s), 3.73 (2H, s), 4.84 (2H, s), 6.88 (2H, d, J=8.7 Hz), 7.09 (2H, d, J=8.7 Hz), 7.37 (2H, d, J=8.0 Hz), 7.56 (2H, d, J=8.0 Hz).

Methyl 3-[[dimethyl-4-(hydroxymethyl)phenylsilyl]methyloxyphenyl]-propionate (5-Scheme 2)

To compound 4-Scheme 2 (29.76 g, 57.8 mmol) was added a solution of acetic acid, THF, water (3:1:1) (500 mL). The resulting mixture was stirred at 45° C. for 24 h under an Ar atmosphere, cooled to room temperature and evaporated to dryness. Purification by flash chromatography (silica, 30% ethyl acetate/hexane) gave 5-Scheme 2 as a white crystaline solid. (16.47 g, 79%): TLC $r_f$ 0.29 (silica 30% ethyl acetate/hexane); $^1$H NMR (400 MHz, $CDCl_3$) δ 0.41 (6H, s), 1.78 (1H, br s), 2.58 (2H, t), 2.88 (2H, t), 3.65 (3H, s), 3.74 (2H, s), 4.69 (2H, s), 6.88 (2H, d, J=8.6 Hz), 7.08 (2H, d, J=8.6 Hz), 7.38 (2H, d, J=7.8 Hz), 7.60 (2H, d, J=7.8 Hz).

Methyl 3-[(dimethyl-4-formylphenylsilyl)methyloxyphenyl]propionate (6-Scheme 2)

To a stirred solution of 5-Scheme 2 (4.0 g, 11.2 mmol) in $CH_2Cl_2$ (150 mL) was added $MnO_2$ (5.0 g, 57.5 mMol). The suspension was heated to reflux under Ar and stirred for 16 h. After cooling to room temperature the reaction mixture was filtered through a pad of celite and rinsed with $CH_2Cl_2$ (50 mL). The filtrate was evaporated to give 6-Scheme 2 as a white crystalline solid. (3.74 g, 94%); TLC $r_f$ 0.47 (silica, 30% ethyl acetate/hexane); $^1$H NMR (400 MHz, $CDCl_3$) δ 0.46 (6H, s), 2.59 (2H, t), 2.89 (2H, t), 3.66 (3H, s), 3.77 (2H, s), 6.88 (2H, d, J=8.5 Hz), 7.09 (2H, d, J=8.5 Hz), 7.78 (2H, d, J=7.9 Hz), 7.86 (2H, d, J=7.9 Hz), 10.03 (1H, s).

Methyl 3-[dimethyl-4-[N-[2-(4-hydroxyphenyl)ethyl]aminomethyl]phenylsilyl]methyloxyphenyl]propionate (7-Scheme 2)

To a stirred solution of methyl 6-Scheme 2 (1.03 g, 2.9 mmol) in dry methanol (30 mL) were added tyramine (0.5 g, 3.6 mMol) and acetic acid (0.22 mL, 3.6 mMol). The reaction was stirred for 2 h, then $NABH_3CN$ (0.23 g, 3.6 mMol) was added portionwise over 15 min. (foaming). After stirring for 16 h the reaction was evaporated to dryness, taken up in $CHCl_3$ (100 mL), washed with brine (100 mL), dried ($Na_2SO_4$) and evaporated. Purification by flash chromatography (silica, 3–5% methanol/$CHCl_3$) gave 7-Scheme 2 as a clear oil. (1.02 g, 74%); TLC $r_f$ 0.20 (silica 5% methanol/$CHCl_3$); $^1$H NMR (400 MHz, $CDCl_3$) δ 0.40 (6H, s), 2.59 (2H, t), 2.75 (2H, t), 2.87 (4H, 2t), 3.66 (3H, s), 3.72 (2H, s), 3.80 (2H, s), 6.69 (2H, d, J=8.4 Hz), 6.87 (2H, d, J=8.6 Hz), 7.01 (2H, d, J=8.4 Hz), 7.08 (2H, d, J=8.6 Hz), 7.27 (2H, d, J=7.8 Hz), 7.53 (2H, d, J=7.8 Hz).

Methyl 3-[[dimethyl-4-[N-[2-(4-hydroxyphenyl)ethyl]acetamidomethyl]-phenylsilyl]methyloxyphenyl]propionate (8-Scheme 2)

To a stirred solution of 7-Scheme 2 (2.0 g, 4.2 mmol) in $CH_2Cl_2$ (50 mL) was added acetic anhydride (0.47 mL, 5 mmol) followed by pyridine (0.81 mL, 10 mmol). After stirring for 16 h the reaction was evaporated to dryness. Purification by flash chromatography (silica, 1–5% methanol/$CHCl_3$) gave 8-Scheme 2 as a white solid. (1.53 g, 70%); TLC $r_f$ 0.41 (silica 5% methanol/ $CHCl_3$); HPLC: Altex Ultrasphere™ Si (4.6×250mm) 1–10% iPrOH/$CHCl_3$ linear gradient over 25 min., UV 280 nm, rt 8.15 min., k' 2.2); $^1$H NMR (400 MHz, MeOH-$d_4$) (amide rotamers) δ 0.37, 0.38 (6H, 2s), 1.91, 2.09 (3H, 2s), 2.55 (2H, t), 2.70, 2.74 (2H, 2t), 2.81 (2H, t), 3.43, 3.45 (2H, 2t), 3.61 (3H, s), 3.74, 3.75 (2H, 2s), 4.44, 4.57 (2H, 2s), 6.69, 6.70 (2H, 2d), 6.83 (2H, d, J=8.6 Hz), 6.96, 6.97 (2H, 2d), 7.05 (2H, d, J=8.7 Hz), 7.17, 7.24 (2H, 2d), 7.57, 7.60 (2H, 2d).

TFA solution cleavage reaction of 8-Scheme 2

To an aliquot of compound 8-Scheme 2 (300 mg, 0.58 mmol) was added TFA (10 mL). The reaction was stirred for 16 h at room temperature and evaporated to dryness. HPLC analysis [Altex Ultrasphere™ SI (4.6×250 mm) 1–10% iPrOH/CHCl$_3$ gradient over 25 min., 1.5 mL/min., UV at 280 and 254 nm] showed only trace amounts of starting material with two major products at rt 3.89 and 15.15 min. The two major products were then isolated by flash chromatography (silica, 2% methanol/CHCl$_3$). The earlier eluting peak (rt 3.89 min.) was identified as methyl 3-(4-hydroxyphenyl)propionate 1-Scheme 3 (95 mg, 91 %); $^1$H NMR (400 MHz, CDCl$_3$) δ 2.50 (2H, t), 2.89 (2H, t), 3.68 (3H, s), 5.78 (1H, br s), 6.76 (2H, d), 7.04 (2H, d). The later eluting peak (rt 15.15 min.) was isolated as a white solid and has a structure consistant with the siloxane dimer 2-Scheme 3 (135 mg, 70%); MS(ES) m/z 669.4 [M+H]$^+$; IR (nujol) 3162, 1616, 1252, 1045 cm$^{-1}$; $^1$H NMR (400 MHz, MeOH-d$_4$) (amide rotomers) δ 0.29,0.30 (6H, 2s), 1.91, 2.09 (3H, 2s), 2.71, 2.72 (2H, 2t), 3.45, 3.46 (2H, 2t), 4.43, 4.56 (2H, 2s), 4.86 (2H, s), 6.69, 6.71 (2H, d, J=7.8 Hz), 6.95, 6.97 (2H, 2d, J=7.8 Hz), 7.13, 7.20 (2H, 2d, J=7.7 Hz), 7.47, 7.50 (2H, 2d, J=7.7 Hz).

HF cleavage reaction of 8-Scheme 2

To compound 8-Scheme 2 (300 mg, 0.58 mmol) in an HF reaction vessel containing anisole (1 mL) was distilled HF (9 mL) while cooling at −78° C. The mixture was stirred for 1 h at 0° C. in an ice bath then evaporated under vacuum to dryness. The residue was placed under high vaccum for several hours to remove excess anisole and analyzed by HPLC. HPLC [Altex Ultrasphere™ SI (4.6×250 mm). 1–10% iPrOH/CHCl$_3$ gradient over 25 min., 1.5 mL/min., UV at 280 and 254 nm] showed a major product with a retention time of 8.87 min. as well as small amounts of the two products 1-Scheme 3 and 2-Scheme 3 isolated in the previous TFA reaction. Purification by flash chromatography (silica 2% methanol/CHCl$_3$) gave the major product as a white solid, identified as the desired cleavage product 3-Scheme 3 and identical with authentic material by TLC, HPLC, MS(ES) and $^1$H NMR (108.5 mg, 69%); MS(ES) m/z 270.4 [M+H]$^+$; $^1$H NMR (400 MHz, CDCl$_3$) (amide rotomers) δ 1.88 and 2.12 (3H, 2s), 2.74 and 2.78 (2H, 2t), 3.41 and 3.58 (2H, 2t), 4.39 and 4.63 (2H, 2s), 6.78 (2H, 2d), 7.95 and 7.01 (2H, 2d), 7.11–7.35 (5H, m).

Dimethyl [dimethyl-4-(triisopropylsilyloxymethyl) phenylsilyl]methyl-malonate (1-Scheme 4)

To a stirred solution of 0.5 M sodium methoxide in methanol (88 mL, 44 mmol) were added dimethyl malonate (10 mL, 85 mmol) followed by 3-Scheme 2 (18.30 g, 44 mmol). The reaction was heated at reflux to 70° C., under Ar, and stirred for 24 h. After cooling to room temperature, the reaction was evaporated to dryness, taken up in ethyl acetate (250 mL), washed with cold aq. 1N hydrochloric acid (250 mL), brine (250 mL), dried (MgSO$_4$) and evaporated. Purification by flash chromatography (silica, 5% ethyl acetate/hexane) gave 1-Scheme 4 as a clear oil. (14.37 g, 70%): TLC r$_f$ 0.34 (silica, 10% ethyl acetate/hexane); $^1$H NMR (400 MHz, CDCl$_3$) δ 0.29 6H, s), 1.09 (18H, d, J=6.5 Hz), 1.18 (3H, m), 1.41 (2H, d, J=7.9 Hz), 3.36 (1H, t), 3.61 (6H, s), 4.83 (2H, s), 7.35 (2H, d, J=7.9 Hz), 7.46 (2H, d, J=7.9 Hz).

Methyl 3-[dimethyl-4-(hydroxymethyl)phenylsilyl] propionate (2-Scheme 4)

Compound 1-Scheme 4 (14.37 g, 30.8 m ol) was added to a solution of (3:1:1) acetic acid, water, THF (200 mL) and heated to 45° C. The reaction was stirred for 24 h, cooled and evaporated to dryness. Purification by flash chromatography (silica, 35% ethyl acetate/hexane) gave the benzyl alcohol as a clear oil. (8.31 g, 87%): TLC r$_f$ 0.40 (silica, 40% ethyl acetate/hexane); ); $^1$H NMR (400 MHz, CDCl$_3$) δ 0.30 (6H, s), 1.42 (2H, d, J=7.7 Hz), 1.66 (1H, br s), 3.35 (1H, t), 3.62 (6H, s), 4.69 (2H, s), 7.36 (2H, d, J=7.9 Hz), 7.49 (2H, d, J=7.9 Hz).

To a stirred solution the above alcohol (8.31 g, 26.8 m ol) in DMSO (50 mL) were added LiCl (2.27 g, 54 mmol) and water (1.4 mL). After flushing with Ar the reaction was heated to 140° C. and stirred for 24 h. The reaction was then cooled to room temperature, taken up in ethyl acetate (250 mL), washed with brine (500 mL), dried (MgSO$_4$) and evaporated. Purification by flash chromatography (silica, 30% ethyl acetate/hexane) gave 2-Scheme 4 as a clear oil. (5.02 g, 74%): TLC r$_f$ 0.41 (silica, 30% ethyl acetate/hexane); $^1$H NMR (400 MHz, CDCl$_3$) δ 0.28 (6H, s), 1.09 (2H, ddd), 1.85 (1H, br s), 2.26 (2H, ddd), 3.62 (3H, s), 4.68 (2H, s), 7.36 (2H, d, J=8.0 Hz), 7.50 (2H, d, J=8.0 Hz).

Methyl 3-[dimethyl-4-(formyl)phenylsilyl]propionate (3-Scheme 4)

To a stirred solution 2-Scheme 4 (1.16 g, 4.6 mMol) in CH$_2$Cl$_2$ (50 mL) was added MnO$_2$ (2.0 g, 23 mMol). The reaction was heated to reflux and stirred for 16 h. After cooling to room temperature the reaction was filtered through a pad of celite, washed with CH$_2$Cl$_2$, and the filtrate evaporated to dryness to give 3-Scheme 4 as a clear oil. (1.03 g, 89%): TLC r$_f$ 0.74 (silica, 30% ethyl acetate/hexane); $^1$H NMR (400 MHz, CDCl$_3$) δ 0.35 (6H, s), 1.12 (2H, ddd), 2.32 (2H, ddd), 3.62 (3H, s), 7.68 (2H, d, J=7.9 Hz), 7.85 (2H, d, J=7.9 Hz), 10.02 (1H, s).

Methyl 3-[dimethyl-4-[N-[2-(4-hydroxyphenyl)ethyl] aminomethylphenyl]-silyl]propionate (4-Scheme 4)

To a stirred solution 3-Scheme 4 (1.00 g, 4 mmol) in MeOH (25 mL) were added tyramine (0.70 g, 5 mmol) followed by HOAc (0.30 mL, 5 mmol). After stirring for 2 h at room temperature NaBH$_3$CN (0.32 g, 5 mmol) was added in portions. The reaction was stirred for 16 h and evaporated to dryness. Purification by flash chromatography (silica, 95:5 to 90:10 CHCl$_3$:MeOH) gave 4-Scheme 4 as an oil. (0.94 g, 61%): TLC r$_f$ 0.25 (silica, 95:5 CHC13:MeOH); $^1$H NMR (400 MHz, CDCl$_3$) δ 0.28 (6H, s), 1.08 (2H, ddd), 2.28 (2H, ddd), 2.77 (2H, t), 2.89 (2H, t), 3.64 (3H, s), 3.81 (2H, s), 6.71 (2H, d, J=8.4 Hz), 7.03 (2H, d, J=8.4 Hz), 7.27 (2H, d, J=7.8 Hz), 7.44(2H, d, J=7.8 Hz).

Methyl 3-[dimethyl-4-[N-[2-(4-hydroxyphenyl)ethyl] acetamidomethyl-phenyl]silyl]propionate (5-Scheme 4)

To a stirred solution of 4-Scheme 4 (0.94 g, 2.4 mmol) in CH$_2$Cl$_2$ (25 mL) were added pyridine (250 μl, 3.1 mmol) followed by acetic anhydride (229 μl, 2.4 mmol). After stirring for 16 h the reaction was taken up in CHCl$_3$ (50 mL) and washed with cold aq. 1N HCl (50 mL), brine (50 mL), dried (MgSO$_4$) and evaporated. Purification by flash chromatography (silica, 98:2 to 95:5 CHCl$_3$:MeOH) gave 5-Scheme 4 as a clear oil. (1.00 g, 95%): TLC r$_f$ 0.41 (silica, 95:5 CHCl$_3$:MeOH); $^1$H NMR (400 MHz, CDCl$_3$) (amide rotamers) δ 0.27 and 0.28 (6H, 2s), 1.07 (2H, m), 1.73 (1H, s), 1.89 and 2.11 (3H, 2s), 2.27 (2H, ddd), 2.76 and 2.79 (2H, 2t), 3.41 and 3.57 (2H, 2t), 3.62 and 3.63 (3H, 2s), 4.38 and 4.61 (2H, 2s), 6.76 and 6.79 (2H, 2d, J=8.4 Hz), 6.96 and 7.01 (2H, 2d, J=8.4 Hz), 7.11 and 7.23 (2H, 2d, J=7.9 Hz), 7.44 and 7.46 (2H, 2d, J=7.9 Hz).

N-[2-(4-Hydroxyphenyl)ethyl]-N-benzylacetamide (3-Scheme 3) from cleavage of 5-Scheme 4

To compound 5-Scheme 4 (300 mg, 0.7 mmol) was added trifluoroacetic acid (20 mL). The reaction was stirred at room temperature for 36 h and concentrated to dryness.

HPLC analysis [Zorbax® SIL (4.6×250 mm) 1–10% iPrOH, CHCl$_3$ gradient over 25 min. UV 280 nm] showed <8% starting material remained. The major product was purified by flash chromatography (silica, 98:2 CHCl$_3$:MeOH) to give 3-Scheme 3 (172 mg, 91%); TLC r$_f$ 0.36 (silica, 95:5 CHCl:MeOH); HPLC: rt 10.75 min. k' 4.4 Zorbax®SIL (4.6×250 mm) 1–10% iPrOH/CHCl$_3$ over 20 min., UV 254 and 280 nm; MS(ES) m/z 270.4 [M+H]$^+$; $^1$H NMR (400 MHz, CDCl$_3$) (amide rotamers) δ 1.88 and 2.12 (3H, 2s), 2.74 and 2.78 (2H, 2t), 3.41 and 3.58 (2H, 2t), 4.39 and 4.63 (2H, 2s), 6.78 (2H, 2d), 7.95 and 7.01 (2H, 2d), 7.11–7.35 (5H, m).

3-[Dimethyl-4-[N-[2-(4-hydroxyphenyl)ethyl] acetamidomethylphenyl]-silyl]propionic acid (1-Scheme 5)

To a stirred solution of 5-Scheme 4 (0.67 g, 1.6 mmol) in dioxane (10 mL) was added aq. 1N NaOH (3.5 mL). After stirring for 16 h the reaction was acidified with aq. 1N HCl (3.5 mL) and partially evaporated. The remaining material was taken up in CHCl$_3$ (75 mL), washed with brine (75 mL), dried (MgSO$_4$) and evaporated to give 1-Scheme 5 as a white solid foam. (0.66 g, 100%): TLC r$_f$ 0.23 (silica, 95:4:1 CHCl$_3$:MeOH:HOAc); 1H NMR (400 MHz, CDCl$_3$) (amide rotamers) δ 0.27 and 0.28 (6H, 2s), 1.07 (2H, m), 1.94 and 2.12 (3H, 2s), 2.28 (2H, ddd), 2.74 and 2.77 (2H, 2t), 3.40 and 3.53 (2H, 2t), 4.36 and 4.58 (2H, 2s), 6.76 and 6.79 (2H, 2d, J=8.4 Hz), 6.93 and 6.99 (2H, 2d, J=8.4 Hz), 7.10 and 7.21 (2H, 2d, J=7.9 Hz), 7.43 and 7.46 (2H, 2d, J=7.9 Hz).

3-[Dimethyl-4-[N-[2-(4-hydroxyphenyl)ethyl] acetamidomethylphenyl]-silyl]pronionyl benzhydrylamine resin (2-Scheme 5)

To BHA resin (obtained from 1.0 g BHA resin hydrochloride after neutralization with a solution of 10% Et$_3$N in CH$_2$Cl$_2$ and washing with CH$_2$Cl$_2$, 1.06 mMol) in a shaker vessel(Stewart et al., *Solid Phase Peptide Synthesis*, Pierce Chemical Company: Rockford, Ill., 1984) were added a solution of 1-Scheme 5 (0.66 g, 1.59 mmol) in DMF (20 mL) followed by HOBt (0.42 g, 3.1 mMol) and DCC (0.36 g, 1.7 mMol). The reaction was shaken for 16 h, washed with DMF (2×25 mL), (1:1) CHCl$_3$:MeOH (2×25 mL), CH$_2$Cl$_2$ (2×25 mL) and dried under vacuum for 24 h to give 2-Scheme 5. (1.36 g): EA %N =2.3 found, 2.4 calc. (0.81 mmol/g), negative Kaiser test.

N-[2-(4-Hydroxyphenyl)ethyl]-N-benzylacetamide (3-Scheme 3) from the solution phase TFA cleavage of 2-Scheme 5

To resin 2-Scheme 5 (301.5 mg, 244 μmol) was added TFA (20 mL). The reaction was stirred for 40 h at room temperature, filtered through a sintered glass funnel and washed with CHCl$_3$ (3×5 mL). The filtrate was evaporated to dryness and dried under vacuum for 24 h to give 3 Scheme 3 as an off white solid identical to the authentic material made in solution. (77.6 mg, 100%, 96% by N analysis of recovered resin): TLC r$_f$ 0.36 (silica, 95:5 CHCl$_3$:MeOH); HPLC: rt 10.75 min. k' 4.4, Zorbax® SIL (4.6×250 mm), 1–10% iPrOH/CHCl$_3$ over 20 min., UV 254 and 280 nm; MS(ES) m/z 270.4 [M+H]$^+$; $^1$H NMR (400 MHz, CDCl$_3$) (amide rotamers) δ 1.88 and 2.12 (3H, 2s), 2.74 and 2.78 (2H, 2t), 3.41 and 3.58 (2H, 2t), 4.39 and 4.63 (2H, 2s), 6.78 (2H, 2d), 7.95 and 7.01 (2H, 2d), 7.11–7.35 (5H, m).

Vapor Phase TFA Cleavage Reaction Studies

To each of four 2 ml sintered glass funnels were placed 100 mg of dried resin 2-Scheme 5. The samples were each washed with CH$_2$Cl$_2$ to swell the resin, then drained mostly dry by vacuum aspiration. Each was then placed into a 50 mL beaker, within a TLC chamber containing a layer of TFA on the bottom. At selected time periods (6, 16, 24 and 40 h) a sintered glass funnel with resin was removed and dried under vacuum to remove residual TFA. The resin in each sintered glass funnel was then washed twice with a 1 ML solution of 2% methanol in CHCl$_3$ filtered directly into separate vials under vacuum. A 5 μl aliquot of each filtrate was then injected into an HPLC and the peak area of the product was obtained to determine the amount cleaved. The conversion factor for the peak area to percent cleaved was obtained from the peak area of the 40 h resin sample and the percent cleaved obtained from nitrogen analysis. For multiple TFA cleavages the washed resin after the 6 h reaction was reintroduced into the TFA chamber for another 6 h and reanalysed as above. This was repeated a third time for another 6 hours. (See FIGS. 1 and 2).

3-[Dimethyl-4-(hydroxymethyl)phenylsilyl]propionic acid

To a solution of 2-Scheme 4 (2.50 g, 9.9 mMol) in dioxane (30 mL) was added aq. 1N NaOH (15 mL). After stirring for 4 h the reaction was acidified with aq. 1N hydrochloric acid (15 mL) and evaporated to near dryness. The residue was taken up in ethyl acetate (100 mL), washed with cold aq. 1N HCl (100 mL), brine (100 mL), dried (MgSO$_4$) and evaporated to give the free acid as a clear oil. (2.36 g, 100%): TLC r$_f$ 0.45 (silica, 95:4:1 CHCl$_3$:MeOH:HOAc); $^1$H NMR (250 MHz, CDCl$_3$) δ 0.30 (6H, s), 1.08 (2H, ddd), 2.30 (2H, ddd), 4.68 (2H, s), 7.36 (2H, d, J=7.9 Hz), 7.50 (2H, d, J=7.9 Hz).

3-[Dimethyl-4-(hydroxymethyl)phenylsilyl]propionyl benzhydrylamine resin (2-Scheme 6)

To BHA resin (obtained from 7.0 g BHA resin hydrochloride after neutralization with 10% Et$_3$N in CH$_2$Cl$_2$ and washing with CH$_2$Cl$_2$, 7.77 mmMol) was added a solution of the above 3-[dimethyl-4-(hydroxymethyl)phenylsilyl] propionic acid (2.36 g, 9.9 mmol) in DMF (30 mL). To this were added HOBt (2.7 g, 20 mmol) and DCC (2.1 g, 9.9 mmol). The reaction was shaken for 16 h, washed with DMF (2×30 mL), (1:1) CHCl$_3$:MeOH (2×30 mL), CH$_2$Cl$_2$ (2×30 mL), hexane (30 mL) and dried under vacuum for 24 h to give resin 2-Scheme 6. (8.66 g, 0.90 mmol/g): negative ninhydrin test; (Kaiser et al., *Anal. Biochem.* 1970, 34, 594–598). MAS $^1$H NMR (500 Mhz) δ 0.20 (6H, Si(CH$_3$)$_2$'s), 1.05 (2H, CH$_2$CON), 2.10 (2H, SiCH$_2$C), 2.80 (1H, HO), 4.52 (2H, OCH$_2$—Ar), 7.22, 7.40 (4H, ArH's).

3-[Dimethyl-4-(bromomethyl)phenylsilyl]propionyl benzhydryl amine resin (3-Scheme 6)

To resin 2-Scheme 6 (1.60 g, 1.44 mmol) in a shaker vessel were added THF (30 mL), CBr$_4$ (0.96 g, 2.88 mmol) and Ph$_3$P (0.76 g, 2.88 mmol). The reaction was shaken for 16 h, washed with THF (2×30 mL), ethanol (2×30 mL), CH$_2$Cl$_2$ (2×30 mL), hexane (30 mL) and dried under vacuum for 16 h to give resin 3-Scheme 6. (1.76 g, 0.84 mMol/g): EA % N found 1.18, calc. 1.22; % Br found 6.62, calc. 6.95.

3-[Dimethyl-4-[N-[2-(4-hydroxyphenyl)ethyl] aminomethylphenyl]silyl]-propionyl benzhydrylamine resin (4-Scheme 6)

To resin 3-Scheme 6 (1.50 g, 1.26 mmoL) in a shaker vessel were added DMF (20 mL), tyramine (1.7 g, 12.4 mmol) and Et$_3$N (1.8 mL, 12.9 mmol). The reaction was shaken for 16 h, washed with DMF (2×20 mL), MeOH (2×20 mL), CH$_2$Cl$_2$ (2×20 mL), hexane (20 mL) and dried under vacuum for 16 h to give resin 4-Scheme 6. (1.52 g, 0.72 mmol/g): EA % N found 2.01 calc 2.33; MAS $^1$H NMR (500 MHz) δ 0.20 (6H, Si(CH$_3$)$_2$'s), 1.10 (2H, CH$_2$CON), 2.20 (2H, SiCH$_2$C), 2.70 (CH$_2$Ar), 2.82 (2H, NCH$_2$C), 3.74 (2H, NCH$_2$Ar), 6.71, 6.90, 7.18, 7.40 (8H, ArH's).

3-[Dimethyl-4-[N-[2-(4-hydroxyphenyl)ethyl] acetamidomethylphenyl]-silyl]propionyl benzhydrylamine resin (5-Scheme 6)

To resin 4-Scheme 6 (1.0 g, 0.72 mMol) in a shaker vessel were added CH$_2$Cl$_2$ (20 mL), pyridine (60 μl, 0.74 mmol) and acetic anhydride (70 μl, 0.74 mmol). The reaction was shaken for 16 h, washed with CH$_2$Cl$_2$ (2×20 mL), MeOH (2×20 mL), CH$_2$Cl$_2$ (20 mL), hexane (20 mL) and dried under vacuum for 16 h to give resin 5-Scheme 6. (1.07 g): MAS $^1$H NMR (500 MHz) (amide rotamers) δ0.19 (6H, Si(CH$_3$)$_2$'s), 1.02 (2H, CH$_2$CON), 1.80, 1.95 (3H, CH$_3$CON), 2.15 (2H, SiCH$_2$C—), 2.63, 2.70 (2H, CH$_2$Ar), 3.29, 3.45 (2H, NCH$_2$C), 4.22, 4.49 (2H, NCH$_2$Ar), 6.70, 6.81, 6.89, 7.3(8H, ArH's). TFA vapor cleavage of this resin 5-Scheme 6 for 72 h at room temperature gave a 72 % isolated yield of 3 Scheme 3, identical by HPLC, TLC, MS(ES) and $^1$H NMR with authentic material. A small amount (<5%) of the diacetylated material was also obtained after cleavage.

3-[Dimethyl-4-[N-[2-(4-N',N'-dimethylaminoethyloxyphenyl)ethyl]acetamido-methylphenyl]silyl]propionyl benzhydrylamine resin (6-Scheme 6)

To resin 5-Scheme 6 (0.87 g, 0.58 mmol) in a shaker vessel were added dry THF (15 mL), N,N-dimethylaminoethanol (0.58 mL, 5.8 mmol), Ph$_3$P (0.76 g, 2.9 mmol) and DIAD (0.57 mL, 2.9 mmol). The reaction was shaken under an Ar atmosphere for 4 h and filtered dry under Ar. The reaction was repeated an additional time for 16 h, washed with THF (2×15 mL), MeOH (2×15 mL), CH$_2$Cl$_2$ (2×15 ml), hexane (15 mL) and dried under vacuum for 16 h to give resin 6-Scheme 6. (0.94 g, 0.67 mmol/g); MAS $^1$H NMR (500 MHz) (amide rotamers) δ 0.21 (6H, Si(CH$_3$)$_2$'s), 1.08 (2H, CH$_2$CON), 1.95,2.05 (3H, CH$_3$CON), 2.19 (2H, SiCH$_2$C), 2.32 (6H, N(CH$_3$)$_2^1$s), 2.72 (2H, ArOCH$_2$C), 2.80 (2H, CH$_2$Ar), 3.36, 3.52 (2H, NCH$_2$C), 4.02 (2H,CCH$_2$N), 4.30, 4.58 (2H, NCH$_2$Ar), 6.80, 6.90, 7.14, 7.47 (8H, ArH's).

N-[2-(4-N',N'-dimethylaminoethyloxyphenyl)ethyl]-N-benzylacetamide (7-Scheme 6)

Resin 6-Scheme 6 (200 mg, 134 μmol) was exposed to TFA vapor at room temperature for 72 h and dried under vacuum. Extraction with (1: 1) CHCl$_3$:MeOH (4×2 mL), evaporation of the filtrate and drying under vacuum for 24 h gave 7-Scheme 6 as its TFA salt. (67.2 mg, 100%): TLC r$_f$ 0.23 (silica, 9:1 CHCl$_3$:MeOH); MS(ES) m/z 341.0 [M+H]$^+$; $^1$H NMR (400 MHz, CDCl$_3$) (amide rotamers) δ 1.92 and 2.12 (3H, 2s), 2.77 and 2.82 (2H, 2t), 2.98 (6H, s), 3.49 (2H, t), 3.58 (2H, m), 4.33 (2H, t), 4.53 and 4.60 (2H, 2s), 6.94 and 6.97 (2H, 2d, J=8.5 Hz), 7.13 and 7.14 (2H, 2d, J=8.5 Hz), 7.19–7.38 (5H, m).

What is claimed is:

1. A method for preparing a resin-bound compound, wherein the compound is an aromatic carbocycle comprising an aromatic carbon atom and at least one substituent, X, A, B or C, said method comprising the steps of:

(i) coupling the aromatic carbon to a polymeric resin support through a silane linker to give a resin-bound aryl silane intermediate of formula (I):

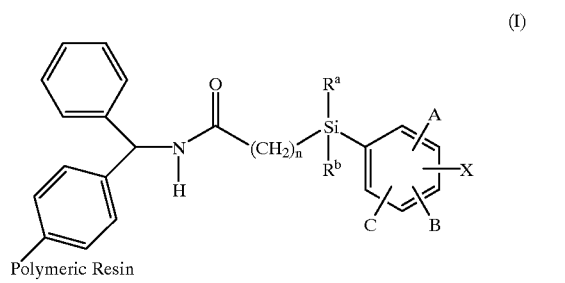

wherein:

R$^a$ and R$^b$, independently from one another, are C$_1$ to C$_6$ alkyl;

X, A, B and C are, independently from one another, hydrogen, halogen, alkyl, alkenyl, alkynyl, alkoxy, alkylthio, C(O)R$^d$, wherein R$^d$ is hydrogen or alkyl, t-butoxyaminocarbonyl, cyano, nitro, aryl, heteroaryl, arylalkyl, alkyl disulfide, aryl disulfide, acetal, fluorenylmethoxycarbonyl or orthoester group; and n is an integer from 2 to 20; and (ii) performing additional synthetic chemistry on at least one substituent, X, A, B or C, in order to modify said substituent, with the proviso that not all of substituents X, A, B or C are hydrogen and not all of X, A, B or C are alkyl.

2. The method of claim 1 wherein the silane linker is —C(O)—(CH$_2$)$_n$—Si—R$^a$R$^b$, wherein R$^a$ and R$^b$ are independently, C$_1$ to C$_6$ alkyl, and n is an integer from 2 to 20.

3. The method of claim 2 wherein R$^a$ and R$^b$ are independently, C$_1$ to C$_4$ alkyl.

4. The method of claim 2 wherein R$^a$ and R$^b$ are both methyl or ethyl.

5. The method of claim 2 wherein R$^a$ and R$^b$ are both methyl.

6. The method of claim 1 wherein n is the integer 3.

7. The method of claim 1 wherein the polymeric resin support is a cross-linked polystyrene resin, a polyethylene glycol-polystyrene resin, or a polypropylene glycol resin.

8. The method of claim 1 wherein after step (ii), the method further comprises the step of cleaving the resin-bound aryl silane intermediate so that the aromatic carbocycle resulting from the cleavage has a hydrogen on the aromatic carbon where it was bound through the silane linker.

9. The method of claim 1 wherein the aromatic carbon is first coupled to the silane linker.

10. The method of claim 8 wherein the aromatic carbocycles are cleaved from the polymeric resin support by treatment with trifluoroacetic acid.

11. A method for preparing a library of diverse resin-bound aromatic carbocycles each comprising an aromatic carbon atom and at least one substituent, X, A, B or C, said method comprising the steps of:

(i) coupling the aromatic carbon atom of each of a plurality of aromatic carbocycles to an individual polymeric resin support through a silane linker to give a plurality of resin-bound aryl silane intermediates of formula (I)

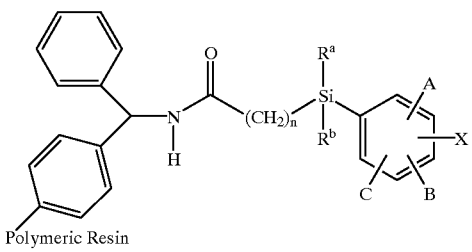

(I)

wherein:

R$^a$ and R$^b$, independently from one another, are C$_1$ to C$_6$ alkyl;

X, A, B and C are, independently from one another, hydrogen, halogen, alkyl, alkenyl, alkynyl, alkoxy, alkylthio, C(O)R$^d$, wherein R$^d$ is hydrogen or alkyl, t-butoxyaminocarbonyl, cyano, nitro, aryl, heteroaryl, arylalkyl, alkyl disulfide, aryl disulfide, acetal, fluorenylmethoxycarbonyl or orthoester group; and n is an integer from 2 to 20;

(ii) optionally dividing said resin-bound aryl silane intermediates into a plurality of portions;

(iii) performing additional synthetic chemistry on at least one of the substituents, X, A, B or C contained on the plurality of aromatic carbocycles, in order to modify said substituent; and (iv) optionally recombining the portions, with the proviso that not all of substituents X, A, B or C are hydrogen and not all of X, A, B or C are alkyl.

12. The method of claim 11 wherein the steps of (ii) dividing the portions, (iii) performing additional synthetic chemistry, and (iv) recombining the portions, are carried out more than once.

13. The method of claim 12, wherein after step (iv), the method further comprises the step of partially cleaving the aromatic carbocycles from the individual polymeric resin supports so that the aromatic carbocycles resulting from the cleavage have a hydrogen on the aromatic carbon where they were bound to the polymeric resin support through the silane linker.

14. The method of claim 13 wherein the derivatized aromatic carbocycles are fully cleaved from the resin.

15. The method of claim 11 wherein the polymeric resin support is a cross-linked polystyrene resin, a polyethylene glycol-polystyrene resin, or a polypropylene glycol resin.

16. The method of claim 14 wherein the aromatic carbocycles are cleaved from the polymeric resin support by treatment with trifluoroacetic acid.

17. The method of claim 11 wherein each of the plurality of aromatic carbocycles is attached to the polymeric resin support by a silane linker comprising —C(O)—(CH$_2$)$_n$-SiR$^a$R$^b$, wherein R$^a$ and R$^b$ are independently, C$_1$ to C$_6$ alkyl, and n is an integer from 2 to 20.

18. The method of claim 17 wherein R$^a$ and R$^b$ are independently, C$_1$ to C$_4$ alkyl.

19. The method of claim 17 wherein R$^a$ and R$^b$ are both methyl or ethyl.

20. The method of claim 17 wherein R$^a$ and R$^b$ are both methyl.

21. The method of claim 17 wherein n is the integer 3.

22. A compound of Formula (I):

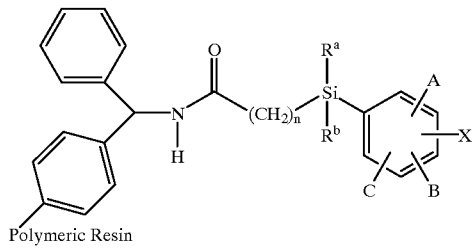

wherein:

R$^a$ and R$^b$, independently from one another, are C$_1$ to C$_6$ alkyl;

X, A, B and C are, independently from one another, hydrogen, halogen, alkyl, alkenyl, alkynyl, alkoxy, alkylthio, C(O)R$^d$, wherein R$^d$ is hydrogen or alkyl, t-butoxyaminocarbonyl, cyano, nitro, aryl, heteroaryl, arylalkyl, alkyl disulfide, aryl disulfide, acetal, fluorenylmethoxycarbonyl or orthoester group, provided that X, A, B and C can not all be hydrogen and X, A, B and C can not all be alkyl; and n is an integer from 2 to 20.

* * * * *